(12) United States Patent
Huffman et al.

(10) Patent No.: US 10,267,734 B2
(45) Date of Patent: Apr. 23, 2019

(54) WAVELENGTH DISPERSIVE MICROSCOPE SPECTROFLUOROMETER FOR CHARACTERIZING MULTIPLE PARTICLES SIMULTANEOUSLY

(71) Applicant: Colorado Seminary, Which Owns and Operates The University of Denver, Denver, CO (US)

(72) Inventors: Donald Ray Huffman, Tucson, AZ (US); John Alexander Huffman, Centennial, CO (US)

(73) Assignee: Colorado Seminary Which Owns and Operates the University of Denver, Denver, CO (US)

( * ) Notice: Subject to any disclaimer, the term of this patent is extended or adjusted under 35 U.S.C. 154(b) by 0 days.

(21) Appl. No.: 15/109,390

(22) PCT Filed: Jan. 7, 2015

(86) PCT No.: PCT/US2015/010418
§ 371 (c)(1),
(2) Date: Jun. 30, 2016

(87) PCT Pub. No.: WO2015/105831
PCT Pub. Date: Jul. 16, 2015

(65) Prior Publication Data
US 2016/0320306 A1    Nov. 3, 2016

Related U.S. Application Data

(60) Provisional application No. 61/925,117, filed on Jan. 8, 2014.

(51) Int. Cl.
*G01N 21/64* (2006.01)
*G01J 3/28* (2006.01)
(Continued)

(52) U.S. Cl.
CPC ............ *G01N 21/6458* (2013.01); *G01J 3/28* (2013.01); *G01J 3/44* (2013.01); *G01N 15/1434* (2013.01);
(Continued)

(58) Field of Classification Search
CPC .................................................. G01N 21/6458
See application file for complete search history.

(56) References Cited

U.S. PATENT DOCUMENTS

| 4,354,114 A | 10/1982 | Karnaukhov et al. |
| 4,918,475 A | 4/1990 | Edwards |

(Continued)

FOREIGN PATENT DOCUMENTS

EP    1912059    4/2008

OTHER PUBLICATIONS

Cheng et al. (Oct. 15, 2010) "Real Time Observations of Chemical Reactions of Individual Metal Nanoparticles with High Throughput Single Molecule Spectral Microscopy," Anal. Chem. 82:20.8744-8749.

(Continued)

*Primary Examiner* — Michael C Bryant
(74) *Attorney, Agent, or Firm* — Neugeboren O'Dowd PC

(57) ABSTRACT

Provided are inexpensive devices and methods for obtaining emission or scattering spectra of multiple particles simultaneously and for characterizing the particles based on their emission or scattering spectra. The disclosed devices and methods are useful for analyzing multiple particles to determine one or more characteristics of the particles, such as size, type, elastic scattering, fluorescence and/or Raman characteristics, for distinguishing between biological and non-biological particles, and for biomedical assaying applications. Laboratory or research grade spectroscopic devices are described. Smartphone-based spectroscopic devices are (Continued)

also described, where various components of a smartphone are used for data collection and analysis purposes.

30 Claims, 23 Drawing Sheets

(51) Int. Cl.
| | |
|---|---|
| *G01J 3/44* | (2006.01) |
| *G01N 21/85* | (2006.01) |
| *G01N 15/14* | (2006.01) |
| *G01N 21/65* | (2006.01) |
| *G01N 21/71* | (2006.01) |
| *G02B 21/16* | (2006.01) |
| *G01N 15/00* | (2006.01) |

(52) U.S. Cl.
CPC ..... *G01N 15/1456* (2013.01); *G01N 15/1463* (2013.01); *G01N 21/6428* (2013.01); *G01N 21/65* (2013.01); *G01N 21/718* (2013.01); *G01N 21/85* (2013.01); *G02B 21/16* (2013.01); *G01N 2015/0065* (2013.01); *G01N 2015/144* (2013.01); *G01N 2015/1465* (2013.01); *G01N 2021/6417* (2013.01); *G01N 2021/6439* (2013.01); *G01N 2201/062* (2013.01); *G01N 2201/0612* (2013.01)

(56) References Cited

U.S. PATENT DOCUMENTS

| | | | |
|---|---|---|---|
| 8,362,435 | B2 | 1/2013 | Bronk |
| 2006/0222567 | A1* | 10/2006 | Kloepfer ............ G01N 21/78 422/68.1 |
| 2006/0279732 | A1* | 12/2006 | Wang ................. G01J 3/02 356/326 |
| 2008/0093566 | A1 | 4/2008 | Reinisch et al. |
| 2010/0213376 | A1* | 8/2010 | Gardner, Jr. ............ G01J 3/02 250/339.07 |
| 2011/0063433 | A1 | 3/2011 | Thonhauser |

OTHER PUBLICATIONS

O'Connor et al. (2014) "Using spectral analysis and fluorescence lifetimes to discriminate between grass and tree pollen for aerobiological applications," Analytical Methods. 6:93.10.1.1633-1639.

Poschl (Nov. 21, 2005) "Atmospheric Aerosols: Composition, Transformation, Climate and Health Effects," Angewandte Chemie International Edition. 44:46.7520-7540.

Roshchina et al. (Nov. 6, 2004) "Autofluorescence of Developing Plant Vegetative Microspores Studied by Confocal Microscopy and Microspectrofluorimetry," Journal of Fluorescence. 14:6.745-750.

Schultz et al. (Feb. 1, 2000) "Single-target molecule detection with nonbleaching multicolor optical immunolabels," Proc. Natl. Acad. Sci. USA. 97:3.996-1001.

Xiong et al. (Apr. 16, 2013) "Highly sensitive sulphide mapping in live cells by kinetic spectral analysis of single Au—Ag core-shell nanoparticles," Nat Communications. 4:1708.

Yamamoto et al. (Dec. 2002) "Broad range observation of particle deposition on greased and non-greased impaction surfaces using a line-sensing optical microscope," Journal of Aerosol Science. 33:12. 1667-1679.

Zhu et al. (Apr. 11, 2013) "Wide-field Fluorescent Microscopy and Fluorescent Imaging Flow Cytometry on a Cell-phone," Journal of Visualized Experiments. 2013.74:50451. pp. 1-5.

International Search Report with Written Opinion, dated Apr. 10, 2015, corresponding to International Patent Application No. PCT/US15/10418.

* cited by examiner

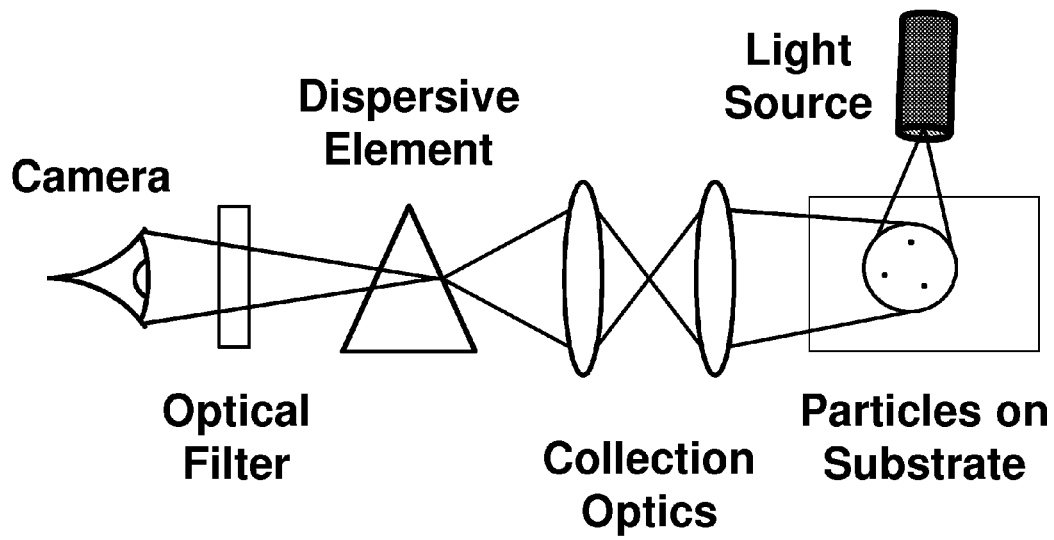
Figure 1B
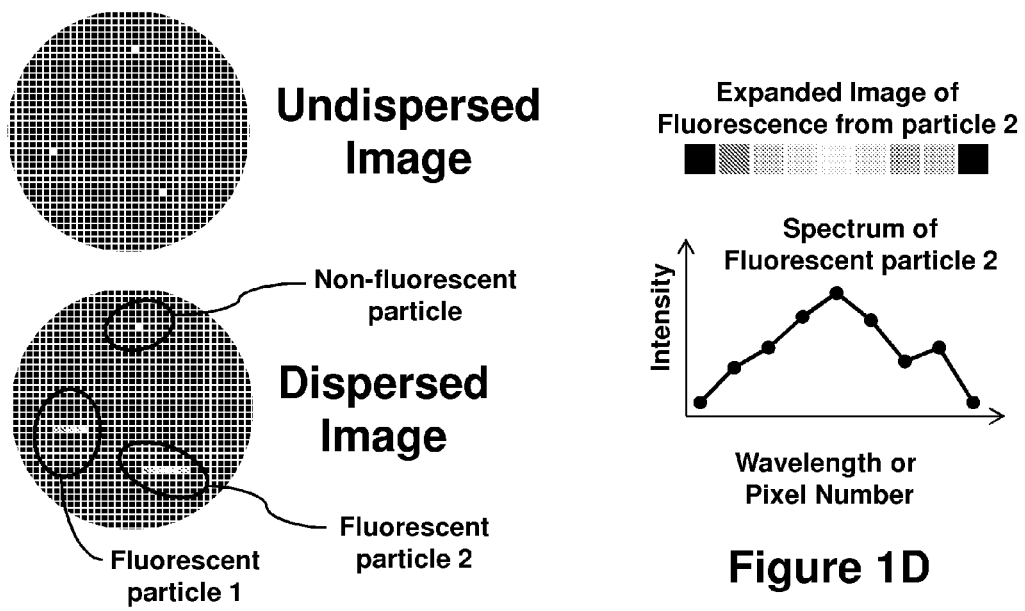
Figure 1C
Figure 1D

Figure 1F
Figure 1G
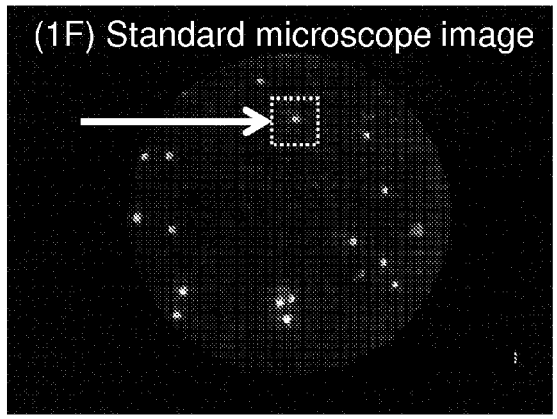
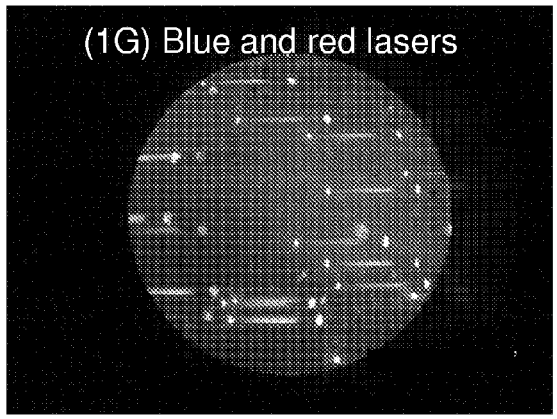
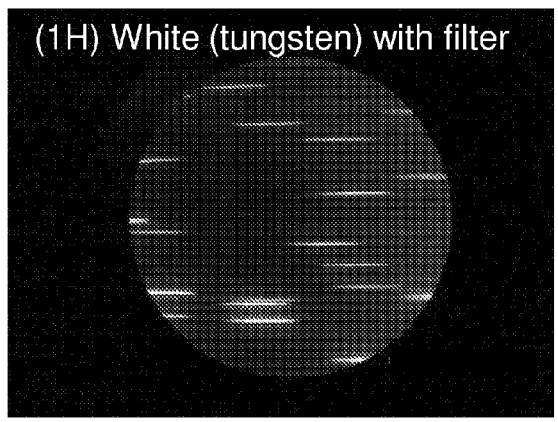
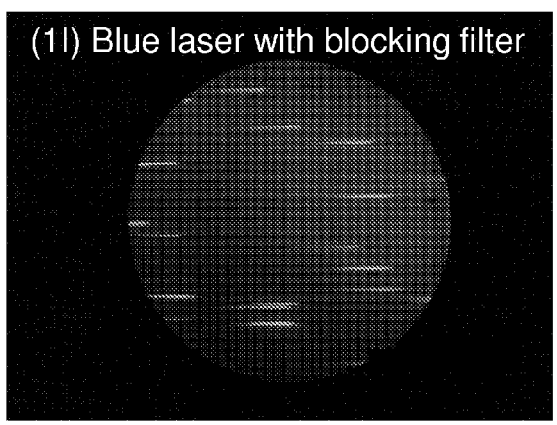
Figure 1H
Figure 1I

Top View — Microscope Slide, Reflection Grating

Fig. 14A
Top View
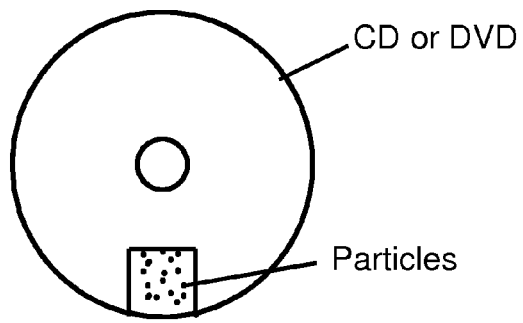
Fig. 14B
Side View
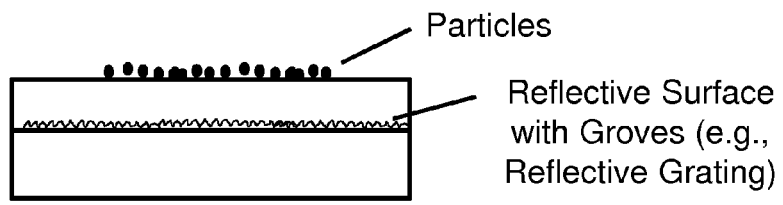
Fig. 14C
Side View
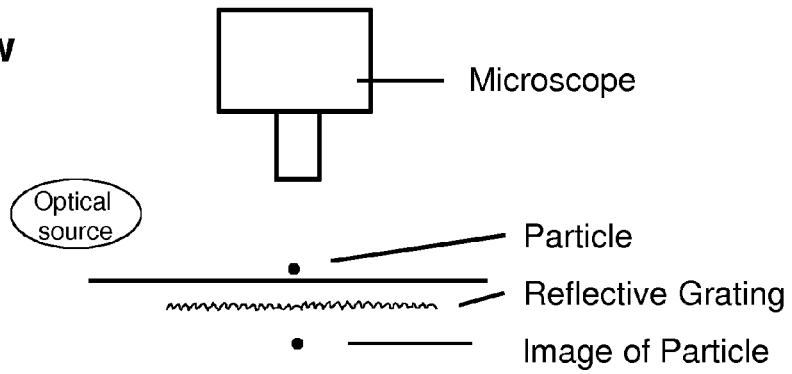
Figure 14

WAVELENGTH DISPERSIVE MICROSCOPE SPECTROFLUOROMETER FOR CHARACTERIZING MULTIPLE PARTICLES SIMULTANEOUSLY

CROSS REFERENCE TO RELATED APPLICATION

This application is a U.S. National Stage Application under 35 U.S.C. § 371 of International Application No. PCT/US2015/010418, filed Jan. 7, 2015, which claims the benefit and priority of U.S. Provisional Application No. 61/925,117, filed Jan. 8, 2014, both of which are hereby incorporated by reference in their entirety to the extent not inconsistent herewith.

BACKGROUND

Many airborne bioparticles can adversely affect human, animal, and agricultural health by acting as allergens and pathogens. Applications of particle detection that have particular importance for health and human safety include monitoring particles in connection with homeland security; moldy homes after water/flood damage; occupational health environments where high human traffic can lead to spread of infectious diseases; areas where seasonal allergies are important; hospital environments where control of pathogen spread is of critical public health importance; and areas where bio-warfare agents may deployed. Airborne bioparticles are also important for diverse natural processes such as the spread and germination of organisms as well as the formation and evolution of clouds.

The importance of particle monitoring sensors for these applications is reflected in the continuous and ongoing development of these devices to improve reliability and throughput, and to enable efficient detection and characterization of particles. For example, currently significant attention is being directed to developing inexpensive and versatile systems capable of characterizing a wide range of biological particles on the basis of optical properties, such as scattering, fluorescence or Raman. As a result, design strategies for providing optical particle classification systems capable of reliable detection and effective implementation for characterization of bioparticles is recognized as a priority in the development of the next generation of these devices.

SUMMARY

The invention relates generally to particle detection methods and devices useful for characterizing spectral properties of multiple particles simultaneously wavelength dispersive element. For example, the invention provides for obtaining emission, scattering or Raman spectra of multiple particles simultaneously and for characterizing the particles based on the obtained spectra. Aspects of the invention involve collecting and analyzing multiple particles to determine one or more characteristics of the particles, such as size, type and fluorescence or elastic scattering characteristics, Raman spectra, or laser-induced breakdown atomic spectroscopy (LIBS). For example, the methods and devices are useful for analyzing environmental hazards, such as determining the presence of unwanted, irritating, or dangerous particles in an environment. For example, aspects of the invention are useful for quickly characterizing whether particles are biological particles or non-biological biological. The invention also provides the ability to distinguish between various types of biological particles, such as determining whether the particles are mold spores, pollen or bacteria and to classify the types of mold, pollen or bacteria present. In addition, the invention provides means for performing biomedical assays, such as to determine whether a protein, antibody or other biomarker is present in a sample and for determining the location and concentration or number density of the biomarkers. For example, the invention provides for the ability to simultaneously distinguish the presence and number of tagged or labeled nanoparticles.

The invention also provides both research-grade and non-research grade devices, benchtop and portable devices, such as devices capable of obtaining detailed spectral characteristics of particles and devices capable of simply determining a presence and/or number of biological or non-biological particles. For example, the invention provides affordable systems which are capable of using the processing, imaging, GPS and/or wireless transmission components of mobile or handheld electronic devices, such as smartphones, for detection and analysis of particle spectra. Providing modular systems, such as where the user provides the processing, imaging and other components of a particle detecting system by using a smartphone, provides one pathway to reduce the cost and complexity of the device in order to place more devices in the field and establish a denser network of particle detecting systems and involve a broader team of scientists, including non-professional or citizen scientists.

In one aspect, the invention provides methods of simultaneously measuring scattering, emission spectra, Raman spectra, or LIBS atomic spectra of a plurality of particles. An exemplary method embodiment of this aspect comprises the steps of: (i) providing the plurality of particles; (ii) exposing the plurality of particles to electromagnetic radiation from an optical source, such that all of the plurality of particles, or all of the particles of interest, are simultaneously exposed to electromagnetic radiation from the optical source, where interactions between each particle and the electromagnetic radiation from the optical source generates scattered or emitted electromagnetic radiation from each particle, such as elastically or inelastically scattered electromagnetic radiation; (iii) collecting and directing at least a portion of the scattered or emitted electromagnetic radiation from each particle onto a wavelength dispersive optical element, thereby generating spatially dispersed scattered or emitted electromagnetic radiation from each particle; (iv) detecting at least a portion of the spatially dispersed scattered or emitted electromagnetic radiation from each particle using an imaging device, such as a digital imaging device, thereby generating an image, such as a digital image, of the spatially dispersed scattered or emitted electromagnetic radiation from each particle; and (v.) analyzing the image to obtain a scattering or emission spectrum of each particle, thereby generating a plurality of scattering or emission spectra corresponding to the plurality of particles. In a method of this aspect, scattered or emitted electromagnetic radiation from only a portion of the particles is collected and/or directed onto the wavelength dispersive optical element, thereby generating spatially dispersed scattered or emitted electromagnetic radiation from only a portion of the particles.

In embodiments, the plurality of particles function as point sources of scattered or emitted electromagnetic radiation, eliminating the need for an entrance slit or aperture. Thus, in embodiments, the method does not include a step of passing the scattered or emitted electromagnetic radiation from each particle through an entrance slit or aperture.

Various methods of the invention comprise, for example, analyzing the image obtained in order to arrive at a spectrum of each particle's scattering or emitted electromagnetic radiation. For certain method embodiments, however, obtaining the spectrum of each particle is optional, and the analyzing step comprises determining whether each particle is fluorescent or non-fluorescent. Determination of the fluorescence state of each particle is beneficial, as it is computationally straightforward to determine whether the particle is fluorescent or not, such as by determining whether the particle appears as wavelength dispersed electromagnetic radiation (fluorescent) or appears as a single point of electromagnetic radiation (non-fluorescent). In embodiments, this technique can be performed by eye or by computer to determine a fraction or percentage of the fluorescent particles. In one embodiment, the analyzing step of the method comprises obtaining a scattering or emission spectrum of each fluorescent particle.

Methods of this aspect are capable of providing a spectrum of each particles, such as a spectrum of the scattered or emitted electromagnetic radiation of each particle expressed as intensity as a function of wavelength. In embodiments, for example, the analyzing step comprises, for each particle, assigning a wavelength value and an intensity value to a plurality of pixels of the image, where each pixel in the plurality of pixels represents detection of spatially dispersed scattered or emitted electromagnetic radiation from the particle.

In embodiments, for conversion of the pixel location to wavelength, one or more reference points are useful to establish an absolute wavelength in the image of the dispersed scattered or emitted electromagnetic radiation. For example, in an embodiment, the analyzing step comprises obtaining one or more additional images of spatially dispersed elastically or inelastically scattered electromagnetic radiation from the plurality of particles and, for each particle, assigning wavelength values to one or more pixel locations corresponding to detection of spatially dispersed elastically or inelastically scattered radiation from that particle, such that one or more wavelength reference points are obtained for each of the plurality of scattering or emission spectra corresponding to the plurality of particles. In this way, for example, the wavelength dispersed image of the scattered or emitted electromagnetic radiation can have reference wavelengths that are assigned.

In embodiments, the wavelength dispersive optical element spatially disperses incident scattered or emitted electromagnetic radiation in one dimension. For example, in a specific embodiment, the step of analyzing comprises, for each particle, determining an intensity value and/or a wavelength value for each of a plurality of pixels in said digital image representing detection of spatially dispersed scattered or emitted electromagnetic radiation distributed along the direction of dispersed electromagnetic radiation.

In an embodiment, the wavelength dispersive optical element is a transmissive wavelength dispersive optical element or a reflective wavelength dispersive optical element provided in optical communication with said particles. In an embodiment, the wavelength dispersive optical element is a transmissive wavelength dispersive optical element provided between the particles and a microscope. In an embodiment, the wavelength dispersive optical element is a reflective wavelength dispersive optical element and said particles are provided between said reflective wavelength dispersive optical element and a microscope.

In embodiments, the resultant scattered or emitted spectrum is normalized to the spectrum of the incident photons and/or to the spectral response of the detector. This allows, for example, a smoother spectrum of scattered or emitted light, free of biases from the optical source or detector. FIGS. 1F-L show examples of this procedure.

Methods and devices of embodiments of the invention are useful for obtaining scattering or emission spectra of multiple particles simultaneously. In embodiments, characteristics such as a particle identity, a particle composition, a particle type, particle size, particle shape, particle morphology, particle optical properties, particle physical properties and any combination of these can be determined. For example, one embodiment of methods of this aspect further comprise comparing the scattering or emission spectrum of each particle with a reference database of scattering or emission spectra of known or standard particles to determine a characteristic of each particle. In certain embodiments, each of the plurality of particles has a size dimension selected from the range of 1 nm to 1 mm, such as a size dimension greater than 1 µm, or a size dimension selected from the range of 1 µm to 500 µm. In embodiments, the particles comprise nanoparticles, such as particles having a size dimension selected from the range of 10 nm to 40 nm. In embodiments, the particles have a size dimension selected from the range of 0.5 µm to 15 µm or from the range of 10 µm to 100 µm. Methods and devices of the invention are useful, for example, for analyzing particles including, but not limited to biological particles and biological particle fragments, pollen and pollen fragments, dust, soot, ash, road dust, mold spores, fungal spores, archae, viruses, algae, cyanobacteria, biological crusts, lichen, bacterial cells, agglomerates and cell fragments, fungal cells, agglomerates and cell fragments, yeast cells, agglomerates and cell fragments, liquid organic particles, solid organic particles, gel-like organic particles, mixed phase organic particles, inorganic particles, mixed composition particles, mineral particles, soil-derived particles, marine-derived particles, sea salt particles, aerosols, fluorescent particles, non-fluorescent particles, manufactured particles, metal nanoparticles, gold nanoparticles, silver nanoparticles, medical assay particles, labeled particles, tagged particles or any combinations of these.

In embodiments, methods, devices and systems of the invention are useful for medical assays. For example in one embodiment, the plurality of particles comprise particles useful in a medical assay, such as metal nanoparticles, gold nanoparticles, silver nanoparticles, medical assay particles, labeled particles, tagged particles or any combinations of these. In one embodiment, multiple assay particles are used. For example, in an embodiment, nanoparticles of a first size, first size distribution or first composition are labeled with a first biomarker, first tag or first antibody and nanoparticles of a second size, second size distribution or second composition are labeled with a second biomarker, second tag or second antibody. In embodiments, these multiple assay particles comprise the plurality of particles used in the devices, systems and methods of the invention, and scattering or emission spectra of the particles are obtained, thus providing for simultaneously detecting the presence and/or number of assay particles and for distinguishing between the different assay particles.

In embodiments, the plurality of particles is provided on a platform, such as a substrate, or in a fluid, such as a liquid or a gas. Useful liquids include, but are not limited to those comprising water, a salt solution, a buffer solution, a bodily fluid, blood, plasma, an organic solvent, an inorganic solvent, a processing chemical or any combination of these. Useful gases include, but are not limited to, those comprising air, oxygen gas, nitrogen gas, water vapor or any combination of these. For certain embodiments where the plurality of particles is provided on a substrate, the particles are collected on the substrate by settling or by impacting said plurality of particles on said substrate. In embodiments, for example, the substrate comprises a transparent substrate, a non-transparent substrate, a coated substrate, an uncoated substrate, a reflective substrate, an opaque substrate. Useful substrates include, but are not limited to those comprising glass, plastic, adhesive, adhesive tape, metal, Teflon, polymer, quartz, diamond, sapphire, a crystal, a particle filter, compact disc (CD), digital video disc (DVD), blu-ray disc, mirror, dispersive element, non-dispersive element, reflective grating, or any combination of these.

Various sources of electromagnetic radiation are useful with the devices and methods of the invention. For example, in embodiments, the optical source comprises a monochromatic source, a narrowband source, a broadband source, a continuous source, a laser, a laser diode, a white light source, a light emitting diode, a synchrotron energy source, sunlight, multiples of these or any combination of these.

In an exemplary embodiment, multiple sources of electromagnetic radiation are utilized, such as in a sequential method where multiple images of scattered or emitted electromagnetic are obtained, for example one image per source. In an embodiment, for example, the particles are sequentially exposed to light from a broad band light source (e.g., a white light source), and one or more laser sources (e.g., a first laser source centered at 405 nm and a second laser source centered at 635 nm), and optionally light from one or more laser diode (LED) light sources. In a specific embodiment the optical source comprises a plurality of sources and the exposing, collecting and directing, detecting and analyzing steps of methods of this aspect are repeated a corresponding plurality of times such that a corresponding plurality of scattering or emission spectra for each particle are obtained, for example, where each of the plurality of scattering or emission spectra for each particle correspond to detection of scattered or emitted electromagnetic radiation generated by one of the plurality of sources. In an exemplary embodiment, two or more sources are utilized and the exposing, collecting and directing, detecting and analyzing steps of methods of this aspect are repeated two or more times such that two or more scattering or emission spectra for each particle are obtained, wherein each of the two or more scattering or emission spectra for each particle correspond to detection of scattered or emitted electromagnetic radiation generated by one of the two or more sources.

In embodiments, there are a variety of ways of characterizing or describing the scattered or emitted electromagnetic radiation generated by the interaction between the electromagnetic radiation from the optical source and the plurality of particles. For example, in one embodiment, the scattered or emitted electromagnetic radiation comprises inelastically scattered electromagnetic radiation. In an embodiment, for example, the scattered or emitted electromagnetic radiation comprises fluorescence or Raman scattered electromagnetic radiation. In another embodiment, for example, the scattered or emitted electromagnetic radiation comprises elastically scattered electromagnetic radiation. In another embodiment, for example, radiation from the interrogated particle is a result of atomic emission from laser induced breakdown spectroscopy (LIBS).

Certain methods of the invention utilize a filter for removing unwanted wavelengths from the scattered or emitted electromagnetic radiation from the plurality of particles. For example, specific embodiments of methods of this aspect further comprise a step of filtering the spatially dispersed scattered or emitted electromagnetic radiation from each particle, in order to generate scattered or emitted electromagnetic radiation from each particle that is optically filtered and spatially dispersed. For example, in embodiments, the detecting step comprises detecting at least a portion of the filtered, spatially dispersed scattered or emitted electromagnetic radiation from each particle using the imaging device, thereby generating the image. In embodiments, the filtering step comprises interacting at least a portion of the scattered or emitted electromagnetic radiation with an optical filter or interacting at least a portion of the dispersed scattered or emitted electromagnetic radiation with an optical filter. Thus, the filter is optionally placed between the dispersing element and the imaging device, between the collection optics and the dispersing element or generally anywhere between the particles and the imaging device. Useful filters include, but are not limited to, a longpass filter, a bandpass filter, a notch filter, an interference filter, a reflective filter, a transmissive filter, a diffraction filter or a dichroic filter. Optical properties of one or more elements of the system (e.g. the camera or lens optics) may limit need for additional filters by reducing transmission of certain wavelengths.

A variety of optical elements are useful with the devices and methods of the invention. For example, in one embodiment, the wavelength dispersive optical element comprises a grating. In some embodiments, for example, the wavelength dispersive optical element comprises a prism. Devices and methods of embodiments of the invention optionally comprise one or more optical elements each independently positioned in optical communication with one or more of the optical source, the particles, the wavelength dispersive optical element and the imaging device. For example, useful optical elements comprise a lens, a mirror, a partial reflector, a filter, a beam splitter, an optical fiber, an optical waveguide, an optical beamguide, a window, an aperture, a slit, a prism, a grating, a reflective grating, a polarizer, a wave plate, a crystal, a beam homogenizer and any combination of these. In certain embodiments, the one or more optical elements each provide for collection, reflection, filtering, transmission, diffraction, refraction or collimation of electromagnetic radiation from the optical source, scattered or emitted electromagnetic radiation from each particle or spatially dispersed scattered or emitted electromagnetic radiation.

In embodiments, the imaging devices useful with the devices and methods of the invention comprise a digital camera or an analog camera. For example, various embodiments include useful digital imaging devices such as those comprising a two-dimensional detector, a CCD sensor or a CMOS sensor. Optionally, the imaging device comprises a monochromatic device, such as a monochromatic sensor. Optionally, the imaging device comprises a color device, such as a color sensor.

In exemplary embodiments, the imaging device comprises a mobile electronic device or a handheld electronic device or a component or peripheral thereof, such as a laptop, a smartphone or a tablet. For example, in certain embodiments, methods of this aspect include where the analyzing step is completed using a mobile electronic device or a handheld electronic device. Optionally, the images obtained by the imaging device are transmitted to a remote computer, a cloud computing system or a distributed computing system using a transceiver of the mobile electronic device or handheld electronic device. For example, in embodiments, the analysis of the transmitted images is completed using the remote computer, the cloud computing system or the distributed computing system.

The invention also provides for systems and devices for simultaneously measuring scattering or emission spectra from a plurality of particles. In one embodiment a device of this aspect comprises: (i) an optical source for generating electromagnetic radiation; (ii) a substrate or fluid (e.g., liquid or gas) volume for providing a plurality of particles, such that the substrate or fluid volume is positioned to receive electromagnetic radiation from the optical source and where interactions between each particle and said electromagnetic radiation from the optical source generates scattered or emitted electromagnetic radiation from each particle; (iii) a wavelength dispersive optical element for generating spatially dispersed scattered or emitted electromagnetic radiation from each particle, where the wavelength dispersive optical element is positioned to receive at least a portion of the scattered or emitted electromagnetic radiation from each particle; (iv) an imaging device, such as a digital imaging device, for generating an image, such as an analog image or a digital image, of the spatially dispersed scattered or emitted electromagnetic radiation from each particle, where the imaging device is positioned to receive at least a portion of the spatially dispersed scattered or emitted electromagnetic radiation from each particle; and (v) a processor, provided in data communication with the imaging device, for analyzing the image corresponding to detection of the spatially dispersed scattered or emitted electromagnetic radiation from each particle and for obtaining a scattering or emission spectrum of each particle, thus generating a plurality of scattering or emission spectra corresponding to the plurality of particles. In system of this aspect, scattered or emitted electromagnetic radiation from only a portion of said particles is collected and/or directed onto the wavelength dispersive optical element, thereby generating spatially dispersed scattered or emitted electromagnetic radiation from only a portion of the particles. In an embodiment, said system comprises a substrate and grating assembly comprising a microscope slide provided in optical communication with a reflective grating. In an embodiment, said system comprises an integrated substrate and a reflective grating, for example, comprising components of a CD or DVD.

As described above with reference to certain methods of the invention, in certain embodiments, devices and systems of embodiments of the invention do not include an entrance slit positioned between the plurality of particles and the wavelength dispersive optical element. For example, each of the plurality of particles functions as a point source of scattered or emitted electromagnetic radiation, and so eliminates a need for an entrance slit.

In exemplary embodiments the imaging device and the processor comprise components of a mobile electronic device or a handheld electronic device, such as a smartphone or a tablet. Certain system and device embodiments comprise, for example, a wireless transmitter, such as a wireless transceiver, providing data communication between the imaging device and the processor. In exemplary embodiments, the imaging device and the wireless transmitter comprise components or peripherals of a mobile electronic device or a handheld electronic device, such as a laptop, a smartphone or a tablet and the processor comprises a remote computer, a cloud computing system or a distributed computing system.

In embodiments, the processor of embodiments of the systems and devices of this aspect of the invention are programmed with instructions. In certain embodiments, the instructions, when executed perform one or more steps of methods of the invention. For example, in one embodiment, the processor is programmed with instructions that when executed determines whether each of the plurality of particles is a fluorescent particle or a non-fluorescent particle. In an embodiment, the processor is programmed with instructions that when executed further obtains a scattering or emission spectra of each fluorescent particle. In an embodiment, for example, the processor is programmed with instructions that when executed assigns, for each of the plurality of particles, a wavelength value and an intensity value to each of a plurality of pixels of the image, where each pixel in the plurality of pixels represents detection of spatially dispersed scattered or emitted electromagnetic radiation from that particle, such as to generate the plurality of scattering or emission spectra corresponding to the plurality of particles. In some embodiments, the systems and devices of the invention also provide for further analysis of the images to determine particle characteristics. For example, in an embodiment, the processor is further programmed with instructions that when executed compares each of the plurality of scattering or emission spectra with a reference database of scattering or emission spectra of known or standard particles to determine a characteristic of each of the plurality of particles.

As with the method embodiments described above, system and device embodiments of this aspect of the invention optionally further comprise one or more optical elements each independently positioned in optical communication with one or more of the optical source, the particles, the substrate, the fluid or liquid, the wavelength dispersive optical element and the imaging device. Useful optical elements include, but are not limited to a lens, a mirror, a partial reflector, a filter, a beam splitter, an optical fiber, an optical waveguide, an optical beamguide, a window, an aperture, a slit, a prism, a grating, a polarizer, a wave plate, a crystal, a beam homogenizer and any combination of these.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1C depicts a schematic illustration of an undispersed image and a dispersed image of detected scattered or emitted light from 3 particles, where the intensity is represented using a grey scale (white is high intensity, black is low intensity). In the top image of FIG. 1C, each particle in the viewing area is represented by a white dot. In the bottom image of FIG. 1C, two fluorescent particles are shown as having a line of various grey shades representing an emission spectrum, and a non-fluorescent particle is shown as a dot without an emission spectrum line.

FIG. 1D provides a schematic illustration of an expanded view of the pixels detected in the image corresponding to dispersed light from a fluorescent particle and a schematic illustration of the spectrum of the fluorescent particle.

FIGS. 1F-1I shows four images of a set of paper mulberry pollen particles deposited onto a glass slide using a bench-top embodiment of the device including a simple point-and-shoot color camera as the detector. FIG. 1F provides a standard microscope image using white light (tungsten filament) illumination and without utilizing a grating or blocking filter, where each dot represents an individual pollen grain. FIG. 1G provides an image of the same particles illuminated with blue (405 nm) and red (~650 nm) lasers, where scattered light is dispersed through a grating to achieve a spectral smear of color to the right of each particle, and illustrates an exemplary mode in which wavelength calibration of the camera pixels is achieved. FIG. 1H provides an image of the same particles illuminated with polychromatic, white light passed through an optical filter blocking wavelengths less than 430 nm, where the spectrum of each particle shows the wavelength dependence of elastic scatter from individual particles. FIG. 1I provides in image of the same particles illuminated with a blue laser, with the scattered radiation passed through an optical filter blocking wavelengths less than 430 nm and represents particle fluorescence without interference from elastic scatter.

FIG. 12A provides results corresponding to *Poa pratensis* using a wavelength dispersive microscope spectrofluorometer incorporating a black and white camera (top plot) and a color camera (bottom plot). FIG. 12B provides results corresponding to Anthoxathuodoratum as reported by O'Connor et al. 2014. The prominent peak at about 680 nm correspondence to chlorophyll, which is not present in the color camera line of the top plot because the poor transmission of these wavelengths.

FIGS. 13, 13A, 13B, and 13C provide images and schematic diagrams showing a system of the invention utilizing a dispersive element comprising a reflection grating provided beneath and in optical communication with a microscope slide serving as a substrate for particles under analysis.

FIGS. 14A-C provide schematics of systems of the present invention using a DVD or CD disc as a substrate and reflective grating. FIG. 14A provides a top view of the CD or DVD having particles on an external surface. FIG. 14B provides a side view showing the particles supported by the external surface of the CD or DVD and also showing the reflective grating component provided in optical communication with the particles. FIG. 14C provides a side view showing incorporation of a microscope provided in optical communication with the CD or DVD so as to receive reflected light from the reflective grating.

DETAILED DESCRIPTION

Figure 1A:
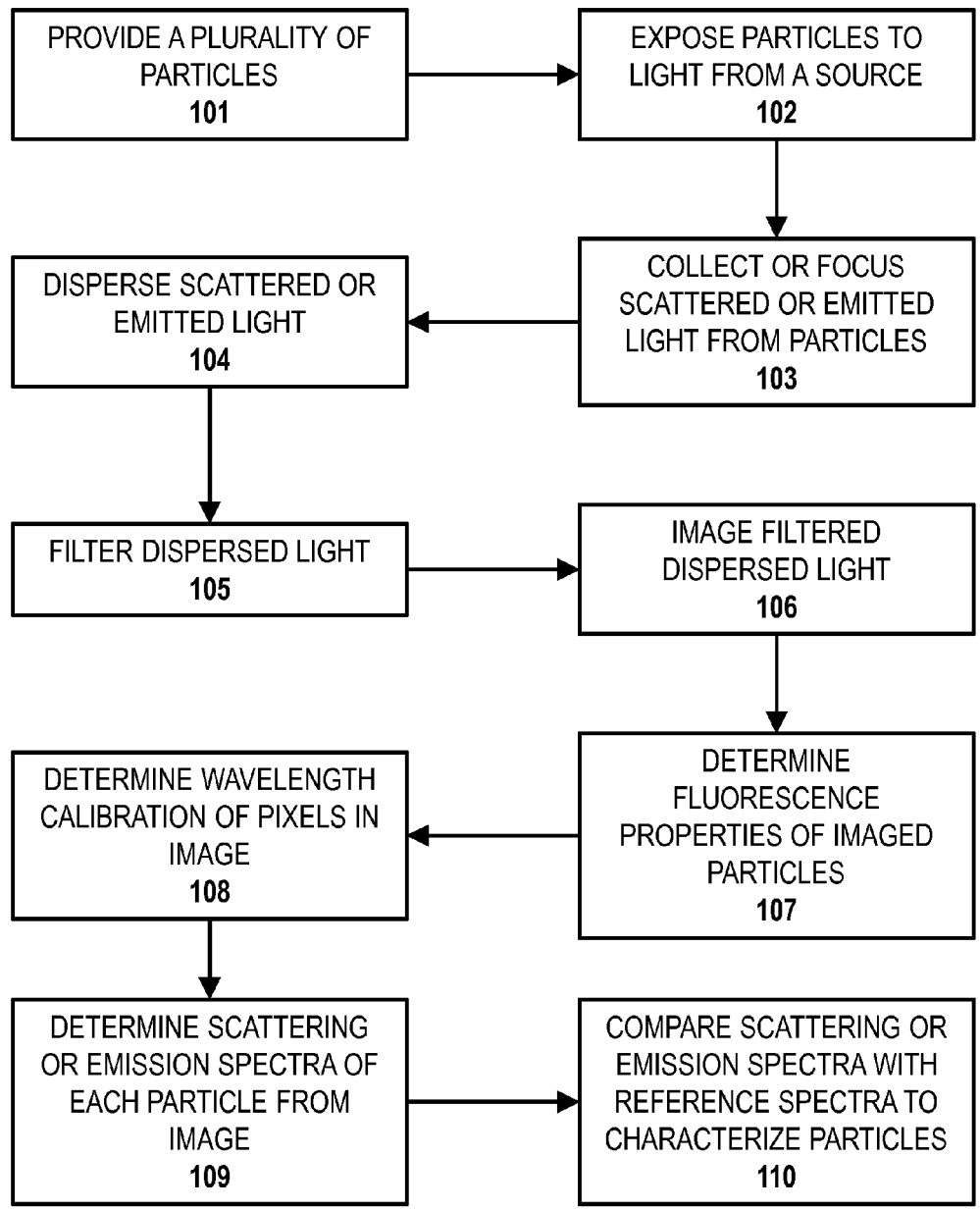
FIG. 1A provides a flow-chart overview of an exemplary method embodiment for obtaining scattering or emission spectra of multiple particles simultaneously and FIG. 1B provides a schematic illustration of a system embodiment for obtaining scattering or emission spectra of multiple particles simultaneously.

In general the terms and phrases used herein have their art-recognized meaning, which can be found by reference to standard texts, journal references and contexts known to those skilled in the art. The following definitions are provided to clarify their specific use in the context of the invention.

"Particles" refer to small objects which can be of natural or anthropogenic origin. In some embodiments, particles include contaminants, such as natural or anthropogenic contaminants. In embodiments, particles can be composed of aggregates of material, such as dust, dirt, smoke, ash, water, soot, metal, salts, minerals, organic materials, liquids, biological materials, or any combination of these or other materials or contaminants. In embodiments, a particle is any material created by the act of friction, for example when two surfaces come into mechanical contact and there is mechanical movement. "Particles" may also refer to biological particles and fragments thereof, for example, pollen, viruses, spores and microorganisms including bacteria, fungi, yeast, archaea, protists, other single cell microorganisms and optionally those microorganisms having a size on the order of 0.5-15 µm. "Particles" may also refer to aerosols. A "particle" may refer to any small amount of condensed material (liquid, solid, or gel), or alternatively may be a small object which absorbs and emits light or scatters light and is thus detectable by measurement of the scattered or emitted light. As used herein, "particle" is intended to be exclusive of the individual atoms or molecules of a carrier fluid or other particle containing media, for example, individual water molecules, oxygen molecules, helium atoms, nitrogen molecules, etc. Specific particles include, but are not limited to, particles having a size selected from 20 nm or greater, 30 nm to 50 nm, 50 nm to 50 µm, a size selected from 100 nm to 10 µm, or a size selected from 500 nm to 5 µm.

The term "electromagnetic radiation" and "light" are used synonymously in the present description and refer to waves of electric and magnetic fields. Electromagnetic radiation useful with the methods and device of the present invention include, but are not limited to, ultraviolet light, visible light, infrared light, or any combination of these light having wavelengths selected from the range of 100 nanometers to 15 microns, and optionally for some embodiments light having wavelengths selected from the range of 300 nanometers to 1000 nanometers. Electromagnetic radiation may include inelastic or elastic scattering and emission, such as fluorescence, phosphorescence or Raman. The term particle is intended to be exclusive of large objects, such as celestial bodies including planets and stars.

"Optical source," "light source" or "source of electromagnetic radiation" refers to a device or device component that is capable of delivering electromagnetic radiation to a sample. The term is not limited to visible radiation, such as by a visible light beam, but is used in a broad sense to include any electromagnetic radiation. The optical source may be embodied as a laser or laser array, such as a diode laser, diode laser array, diode laser pumped solid state laser, LED, LED array, gas phase laser, solid state laser, sunlight, or a lamp or broadband source, to name a few examples.

"Two-dimensional detector" refers to an optical detector capable of spatially resolving input signals (e.g., electromagnetic radiation) in two dimensions across an active area of the detector. A two-dimensional detector is capable of generating an image, for example an image corresponding to an intensity pattern on the active area of the detector. A specific two-dimensional detector embodiment comprises an array of individual detector elements, also referred herein as pixels; for example: a two-dimensional array of photodetectors, a charge-coupled device (CCD) detector, a complementary metal-oxide-semiconductor (CMOS) detector, a metal-oxide-semiconductor (MOS) detector, an active pixel sensor, a microchannel plate detector, a two-dimensional array of photomultiplier tubes, a two-dimensional array of photodiodes, a two-dimensional array of phototransistors, a two-dimensional array of photoresistors, or a photoconductive film.

"Optical communication" refers to components which are arranged in a manner that allows light to transfer between the components.

"Fluid" refers to substances which flow, such as a flow induced by application of a force or application of pressure. Fluids include liquid substances or mixtures, such as water, aqueous solutions, organic solvents, inorganic solvents. Fluids also include gaseous substances or mixtures, such as air, water vapor, oxygen gas and nitrogen gas.

FIG. 1A provides an overview of an exemplary method embodiment for obtaining scattering or emission spectra of multiple particles simultaneously and FIG. 1B provides a schematic illustration of a system embodiment for obtaining scattering or emission spectra of multiple particles simultaneously. First, a plurality of particles is provided for analysis (101). The particles are optionally provided on a substrate or in a fluid, such as a liquid or gas. The particles are optionally collected using a variety of collection methods, including settling or impaction type methods. The particles are then exposed to light from an optical source (102), such as from a laser, LED or white light source, resulting in the generation of scattered or emitted light from each of the exposed particles. A portion of the scattered or emitted light is optically collected (103) by a light collection system and directed onto a wavelength dispersive (104) element to disperse the scattered or emitted light. The wavelength dispersive element (104) may be transmissive or reflective. The dispersed scattered or emitted light is optionally filtered, such as using an optical filter to remove elastically scattered light having the same wavelength as the optical source (105). The dispersed light, optionally filtered, is then imaged using an imaging device (106), such as a digital camera, smartphone camera, CCD or CMOS detector. Since each particle is effectively imaged as a point source, there is no need for an entrance aperture or slit between the particles and the collection optics or camera. The image of the dispersed light is then optionally analyzed to determine whether the particles are fluorescent or non-fluorescent (107). This initial level of analysis optionally provides sufficient information for certain applications, such as to determine the number or percentage of fluorescent or biological particles in a particle sample. For analysis of the scattering or emission spectra of the particles, one or more reference wavelength pixels in the image of the dispersed light are optionally determined (108), such as by determining the pixel location of known wavelengths in the imaged dispersed light. The scattering or emission spectra of each particle is then determined from the image (109). Optionally, the scattering or emission spectra are compared with one or more reference spectra to determine a characteristic of the particle, such as a particle type or size. Optionally, the scattering or emission spectra are normalized to the optical source and/or detector wavelength response curves.

The top image of FIG. 1C depicts a schematic illustration of a digital image of undispersed scattered or emitted light from the three particles shown in FIG. 1B, such as would be imaged in the absence of the dispersive element. The bottom image of FIG. 1C depicts a schematic illustration of a digital image of dispersed scattered or emitted light from the three particles shown in FIG. 1B and identifies one particle as a non-fluorescent particle and two particles as fluorescent particles. FIG. 1D provides a schematic illustration of an expanded view of the imaged dispersed light from the second fluorescent particle. The imaged dispersed light from the second fluorescent particle is converted to a spectrum depicted as a plot of intensity versus pixel number or, alternatively, wavelength.

Figure 1E:
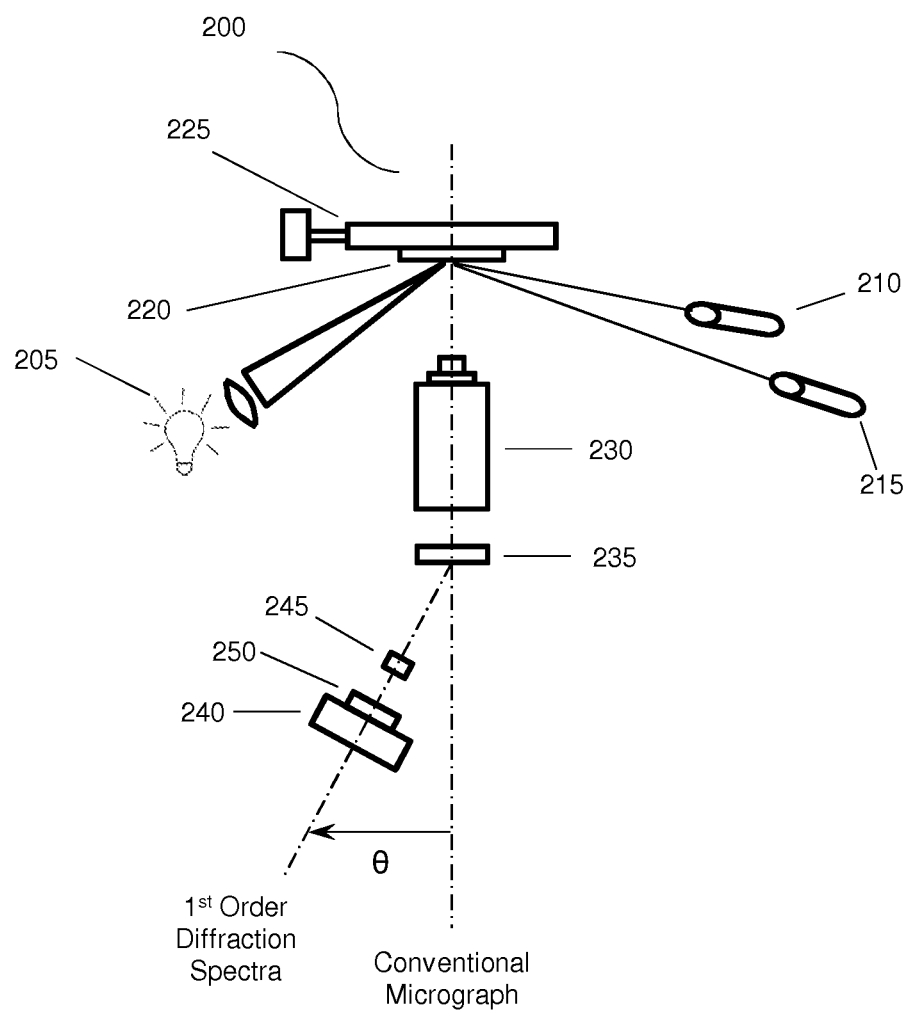
FIG. 1E provides a schematic diagram showing a simultaneous multi-particle fluorescence/scattering spectrometer.

FIG. 1E provides a schematic diagram showing a simultaneous multi-particle fluorescence/scattering spectrometer (200) for use in the systems and methods of the present invention. As shown in FIG. 1E light source comprising one or more of a white light source (205), a 405 nm laser diode (210) and a 650 laser diode, for example, (215) is positioned in optical communication with a substrate (such as a glass slide in FIG. 1E) (220) provided on an X-Y stage (225) so as to illuminate particles provided on an external surface of the substrate, thereby generating light scattered and/or emitted by the particles. Other light sources useful in some embodiments include excitation using a LED source at 330-380 nm and/or 270 nm. A portion of scattered or emitted light from the particles is collected by a light collection system represented here by an objective lens and microscope tube (230) and directed onto a wavelength dispersive element (235), thereby generating dispersed light which is imaged using a digital camera (240). Optionally, the dispersive element may be located under the particle substrate or may be used as the substrate surface. Optionally, the dispersed scattered or emitted light is passed through a wavelength blocking filter (245) to remove elastically scattered light having the same wavelengths as the light source and/or to remove IR light. Light is collected via the camera lens (250) by the digital camera or other detector (240) and is subsequently analyzed to determine scattering or emission spectra corresponding to each of the particles illuminated, which may be optionally compared with one or more reference spectra to determine a characteristic of the particle, such as a particle type or size.

FIGS. 1F-1I provide various images of mulberry pollen particles. FIG. 1F provides an image of the particles obtained with the camera arm of the benchtop apparatus of FIG. 1E at zero degrees. This corresponds to the configuration for the apparatus functioning as an ordinary microscope. In FIGS. 1G through 1I, the camera arm is swung to the position that makes possible detection of the first order diffraction produced by the transmission grating. FIG. 1G provides an image of the spectra of particles obtained using a wavelength dispersive microscope spectrofluorometer with illumination using light from blue and red lasers. On either side of spectral swaths showing fluorescence of the respective particles occur a red dot (on the left) and a blue dot (on the right) which is overexposed and appears white. The blue and red dots are at diffracted positions corresponding to known wavelengths for the blue and red diode lasers, and are thus used to calibrate the wavelength scale of each particle's diffracted image. This, along with the fact that the grating produces wavelength dispersion which is linear in angle, permits a calibration of each spectrum on a wavelength scale. FIGS. 1G, 1H, and 1I are all done with the same detector angle. FIG. 1H provides an image of the particle spectra obtained using the same wavelength dispersive microscope spectrofluorometer with illumination by light from a white light source (tungsten lamp). Analysis of each particle's spectrum using the wavelength calibration from FIG. 1G provides a spectrum of the elastically scattered light intensity as a function of wavelength. FIG. 1I provides an image of the particle spectra obtained using the same wavelength dispersive microscope spectrofluorometer with illumination by light from a blue laser. The result is the spectral intensities of fluorescence (inelastically scattered) by each particle. A filter that blocks the very intense excitation light from the laser at 405 nm permits a cleaner image, devoid of general blue light which would otherwise tend to dominate the image of 1I. The same 405 nm blocking filter is also used in FIG. 1H to make the two images, 1H and 1I, comparable in spectral transmission, a situation which makes more realistic any possible normalization of the fluorescent spectrum of FIG. 1I by the scattered light signal of FIG. 1H.

The dimensions of the spectral swaths shown in FIGS. 1G-1I are dependent on the physical geometric parameters of the apparatus. The swath will be longer if the camera is placed farther from the grating. In some embodiments, for example, during normal operation the swath may be kept at 10% or more of the viewable window, however, this value is adjustable and can be as long or as short as desired depending on application. The longer the swath, the more resolution the spectrum will provide. The vertical extent of the swath is defined mostly by the width of a particle and the magnification applied by the microscope and optics. The number of pixels per swath is dependent on the size the swath takes on the detector sensor and the resolution of the detector. For example, if a detector CCD has more pixels (e.g. 5 megapixels versus 1 megapixel) the swath will be more highly resolved. The range of pixels desired in the x-dimension for a full spectrum may be anywhere from 10 to 1000 (or more for some applications), and in the y-dimension from 1 to 100 (for a ~10 micron particle, and more for larger particles).

Figure 1J:
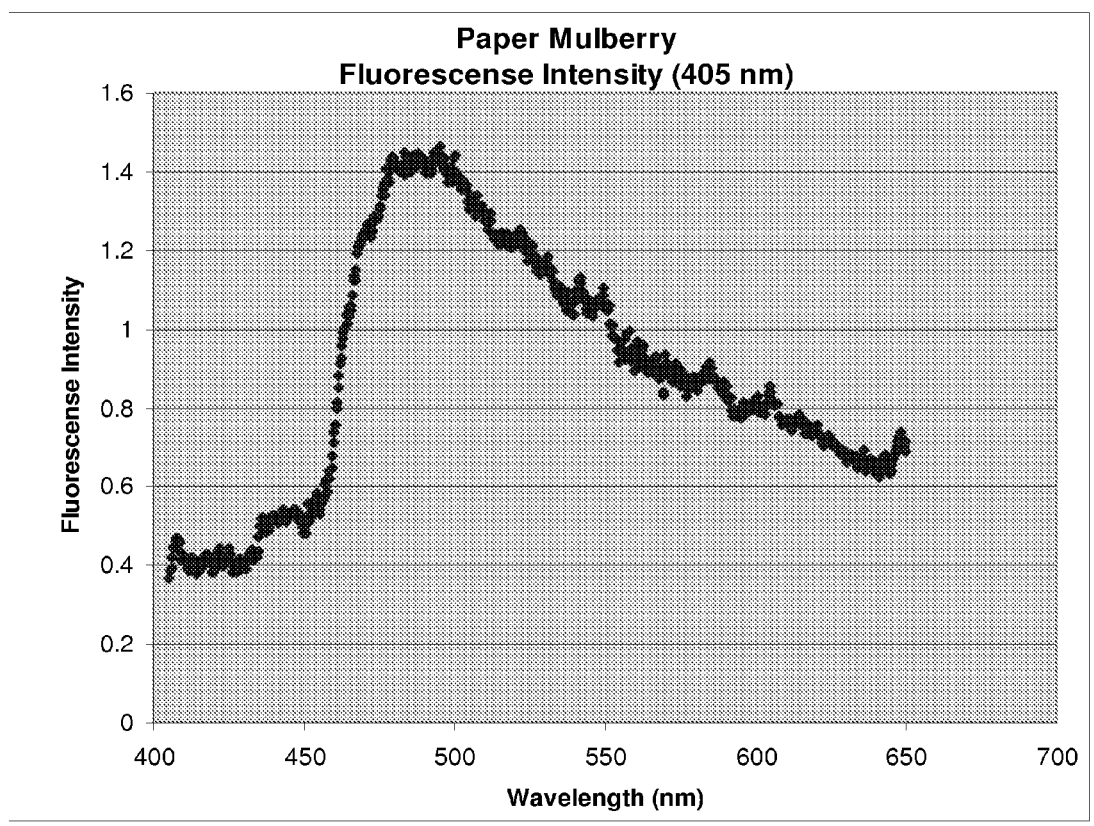
FIG. 1J provides a fluorescence spectrum of a particle excited at 405 nm using the present systems and methods.
Figure 12A:
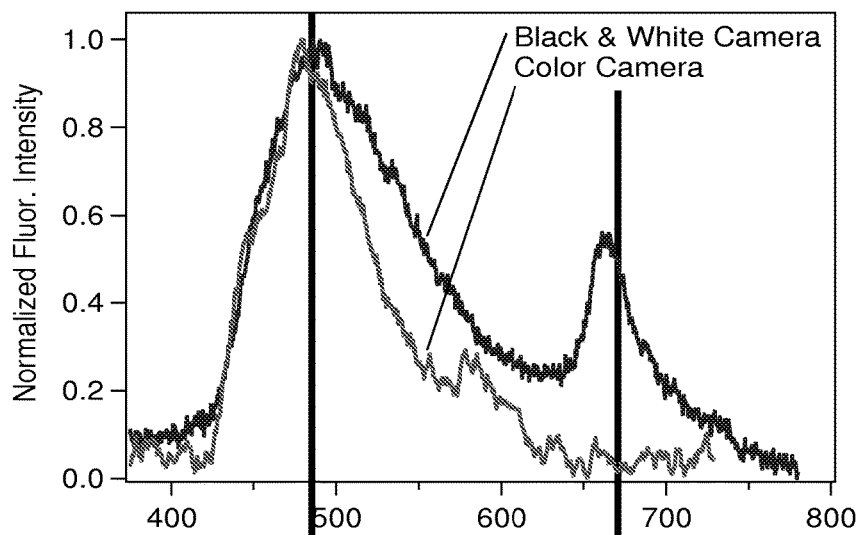
FIGS. 12A and 12B provide spectra of grass pollen particles.
Figure 12B:
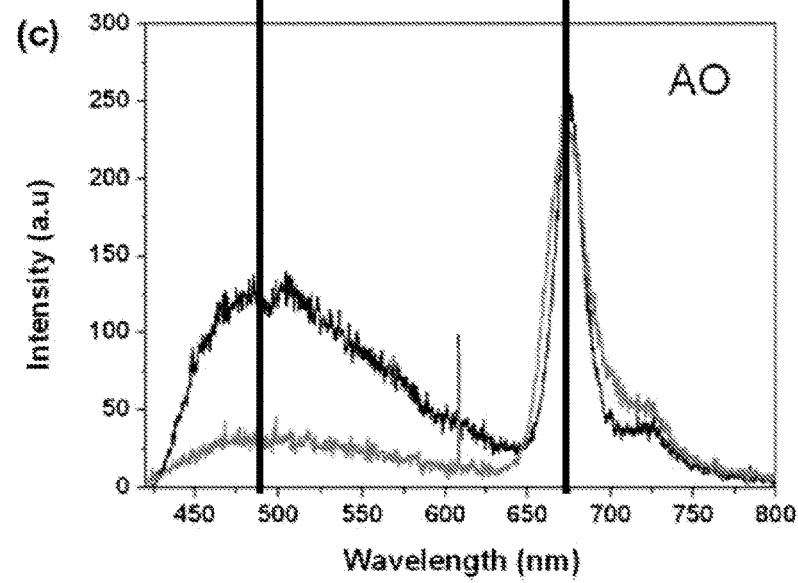

FIG. 1J provides a fluorescence spectrum of a particle excited at 405 nm using the present systems and methods. Fluorescence intensity is plotted as a function of wavelength (nm). The spectrum is characterized by a peak at approximately 490 nm, is an example of a fluorescence spectrum for a biological particle with characteristic broad peak between 450 and 550 nm. The high background is a result of optical interference. The spectrum was acquired with excitation wavelength of 405 nm, utilizing a <430 nm blocking filter to remove elastically scattered light. Another example of particle spectrum is found in FIG. 12.

Figure 1K:
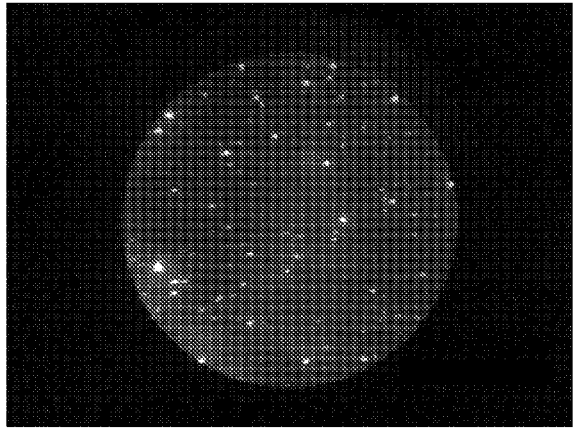
FIGS. 1K-1M provide various images of particles collected from an outdoor air sample.
Figure 1L:
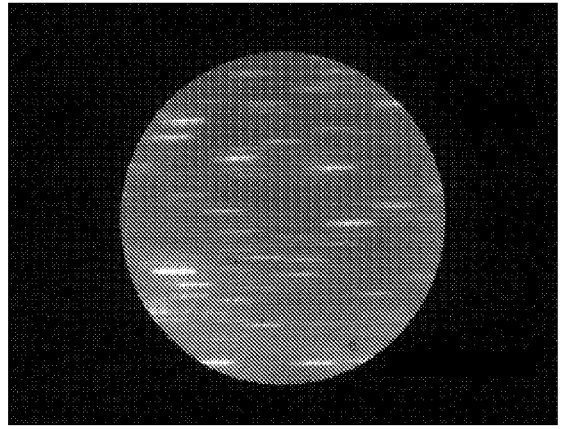
Figure 1M:
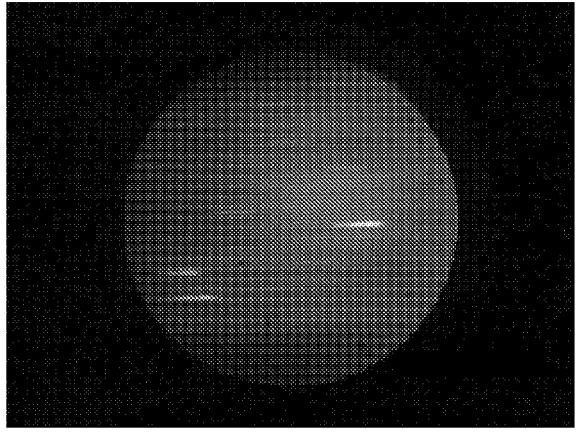

FIGS. 1K-1M provide various images of particles collected from an outdoor air sample. FIG. 1K is an optical micrograph of the particles taken with the detector arm at zero degrees. FIGS. 1L and 1M are taken with the detector arm at the position for first order diffraction from the grating. FIG. 1L provides an image of the particles obtained using light from a white light source (tungsten) showing the elastic scattering spectra of the particles. FIG. 1M provides a fluorescence image of the particles taken with 405 nm laser diode excitation and a laser blocking filter between the grating and the camera. The sample was taken by leaving the microscope slide outside for a period of about 24 hours. FIG. 1L shows elastic scattering from all particles, both fluorescent and non-fluorescent, while FIG. 1M shows only about 3 particles that are fluorescent and thus presumably biological. This series shows the value of the present instrument in easily quantifying both the total number of particles and the number of fluorescent particles. Alternatively, one can use the number for total and for fluorescent particles to calculate the ratio of fluorescent (presumably biological) to the number of non-biological particles.

Figure 1N:
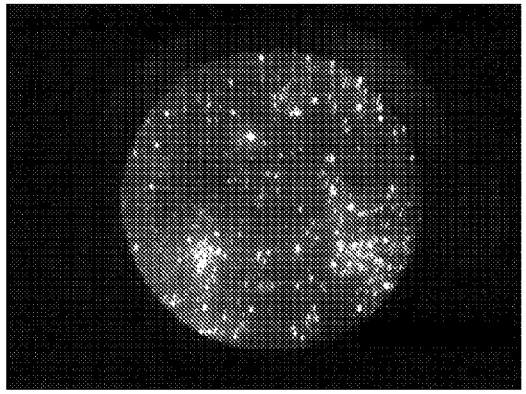
FIGS. 1N-1P provide various images of non-biological and non-fluorescent silca particles.
Figure 1O:
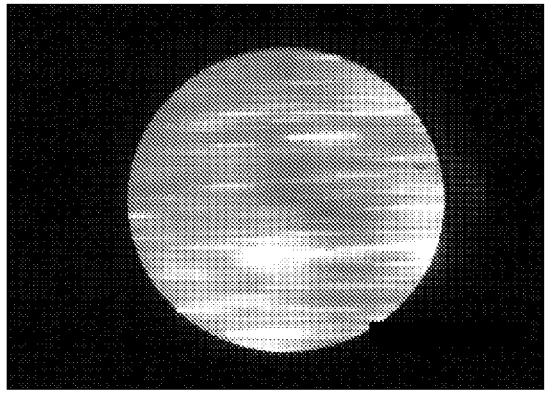
Figure 1P:
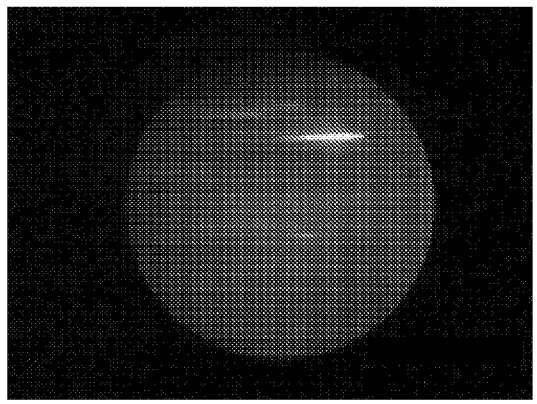

FIGS. 1N-1P provide various images of non-fluorescent silica particles produced by vigorous grinding in an agate mortar of fused silica optical window material used for visible and uv transmission optics. FIG. 1N is an optical micrograph of the particles taken at the zero degree detector angle. FIG. 1O is an image of scattered light spectra of the particles obtained using light from a white light source. FIG. 1P provides fluorescence spectra of the particles using excitation with light at 405 nm. Since the original fused silica material is non-fluorescing, one might expect the very large number of total particles revealed in FIG. 1O to have no corresponding fluorescent images in FIG. 1P. The presence of only a very few fluorescent particles out of the large number of total particles is likely due to contamination from a few fluorescent particles during the particle preparation and measurement procedures. This example illustrates the value of the invention for detecting minor concentrations of probable biological contaminant particles in particulate samples consisting of supposed non-biological particle collections.

The invention may be further understood by the following non-limiting examples.

Example 1: A Wavelength Dispersive Microscope Spectrofluorometer for Measuring Multiple Particles Simultaneously In the late 1800s an objective prism telescope was used to record spectra of multiple stars simultaneously with a wavelength-dispersive prism mounted in front of the telescope objective lens. It was used primarily for multiple stars as in star clusters; in contrast, this Example describes measurement of fluorescence or elastic scattering spectra of multiple small particles, for example, collected on a microscope slide.

Fluorescence spectrometers are in common use to determine spectral fluorescence of bulk solids or collections of many particles. Fluorescence microscopes are also heavily used to look at intensity of fluorescence emission within broad wavelength bands. These are fundamentally not dispersive instruments and thus do not provide emission spectra of particles. Confocal fluorescence microscopes are commonly used to measure fluorescence spectra of individual points on a given particle, but the procedure to analyze multiple particles is time-consuming. The methods and systems of this Example, however, characterizes scattering or emission of individual particles in a collection, and enables any selected particle (or particles) to have full fluorescence, elastic scatter, or Raman spectra determined. In addition, this Example describes an important capability of determining, at a glance by eye or through software, the numbers of fluorescent and non-fluorescent particles.

This Example describes two related tiers of devices. The first is roughly considered the "research instrument," and the second is considered the "smartphone instrument." Both follow the same basic scientific approach, and will be introduced together, but are physically manifested uniquely.

The present invention enables an (i) inexpensive instrument capable of (ii) simultaneously characterizing fluorescence (iii) emission spectra from (iv) many individual particles, each at (v) several excitation wavelengths.

The five components highlighted above are of interest, for example, with the devices and methods of the present invention. There are, for example, some prior instruments that feature one or more of these aspects, but none that combine all five for the unique ability to investigate small particles.

The present invention is optionally used at relatively low magnification to examine a collection of many particles in the field of view for immediate analysis and identification, either by visually counting or using computer analysis. While comparing the multiple scattering or emission spectra of individual particles with a database provides a powerful method of identification, a first level of discrimination can be made immediately by the user. For example, excitation wavelengths are optionally chosen to highlight fluorophores, such as from within biological materials, and so to a high degree of certainty a user can determine whether a particle is biological or not simply by whether the particle fluoresces at all (e.g. whether the particle appears in the camera image as a single dot or as a rainbow smear of color). In this way, even without computational analysis, the instrument provides a simple and inexpensive technique for roughly discriminating between biological and non-biological material.

Additionally, through inclusion of an automatic particle impaction system the device is optionally constructed as an autonomous, unattended particle sampler for sampling long periods of time in remote environments, or for background monitoring by non-professionals in home environments (e.g. for detection of mold spores or allergenic pollen grains). These aspects magnify the utility of this invention. One embodiment for autonomous operation comprises impacting airborne particles by pumping air onto a moving tape. The tape moves at a rate, such as a rate set by the user, slow enough to collect sufficient particles in the desired environment. Once sufficient particle numbers are collected, the excitation optics are turned on, such as for a few seconds, in order to record wavelength calibration values and spectra of emission or scattering. Then the light sources are turned off for a period of minutes to hours until enough particles have been collected at the next impaction spot.

Various instrument embodiments provide, for example, for inexpensive, rapid detection of airborne biological particles (e.g. bacteria, fungal spores, pollen). These aspects are important in two broad areas of science: (1) human health and (2) environmental science.

For example, many airborne bioparticles can adversely affect human, animal, and agricultural health by acting as allergens and pathogens. Currently, much effort is underway to rapidly detect airborne bioparticles that could have important impacts in locations such as: moldy homes after water/flood damage; occupational health environments where high human traffic can lead to spread of infectious diseases; areas where seasonal allergies are important; hospital environments where control of pathogen spread is of critical public health importance; and areas where agents of biological warfare are particular threats.

Additionally, bioparticles are also considered to be potentially major contributors to ice cloud formation and evolution, although the physical processes and dynamics involved are poorly understood. Predicting properties of cloud formation and evolution, for example, may aid in the reduction of uncertainty bars in predicting radiative energy forcing balances that define climate change or global warming issues. Further, precipitation may be significantly affected by changes in ground-cover due to the number and type of biological ice nucleators that are lofted into the atmosphere. Thus, understanding the chemical, physical, and biological processes involved in biological ice nucleation may be important to understanding changes in precipitation in many world ecosystems.

To understand these various areas in more detail scientists have been limited by the ability to detect and characterize biological particles. The research-grade embodiment is thus useful, for example, in research laboratories around the world, such as those particularly interested in the above effects. The smart-phone embodiment, however, provides for magnification of an understanding of these effects by radically increasing the magnitude of data gathered from widely disparate geographic locales, either by employing multiple devices by individual researchers or by employing interested citizen or amateur scientists for increased data collection.

The devices and methods described herein have the potential to not only transform the ability of scientists to gather critical data on health and environmental concerns, but are also useful as important tools for a variety of other health concerns. For example, the detection of outdoor pollen levels is remarkably rudimentary and time-consuming. Pollen alerts listed in public newspapers often utilize very few data from manually observed microscope images of collected samples that result in error-prone models. The ability to rapidly detect and classify pollen with a device inexpensive enough to deploy by the hundreds may transform the collective ability to predict, and even mitigate, pollen allergies. The same is true of mold spore detection that causes serious health problems in sensitized individuals and can be particularly dangerous after home floods, for example. Lastly, the device concepts described herein are also broadly applicable in other medical diagnoses. For example, the devices described herein are able to quickly provide information about the numbers (and type) of fluorescent or light-scattering particles in a complex matrix. Any analysis utilizing such information could benefit from the cheap, simple nature of the smartphone embodiment of the invention. For example, the analysis of blood for the presence of contaminants is optionally used in a clinical setting to provide rapid first screening of patients, saving all parties time and money. Although only a limited number of applications are described herein, the devices of the invention are useful for any other applications.

Figure 3:
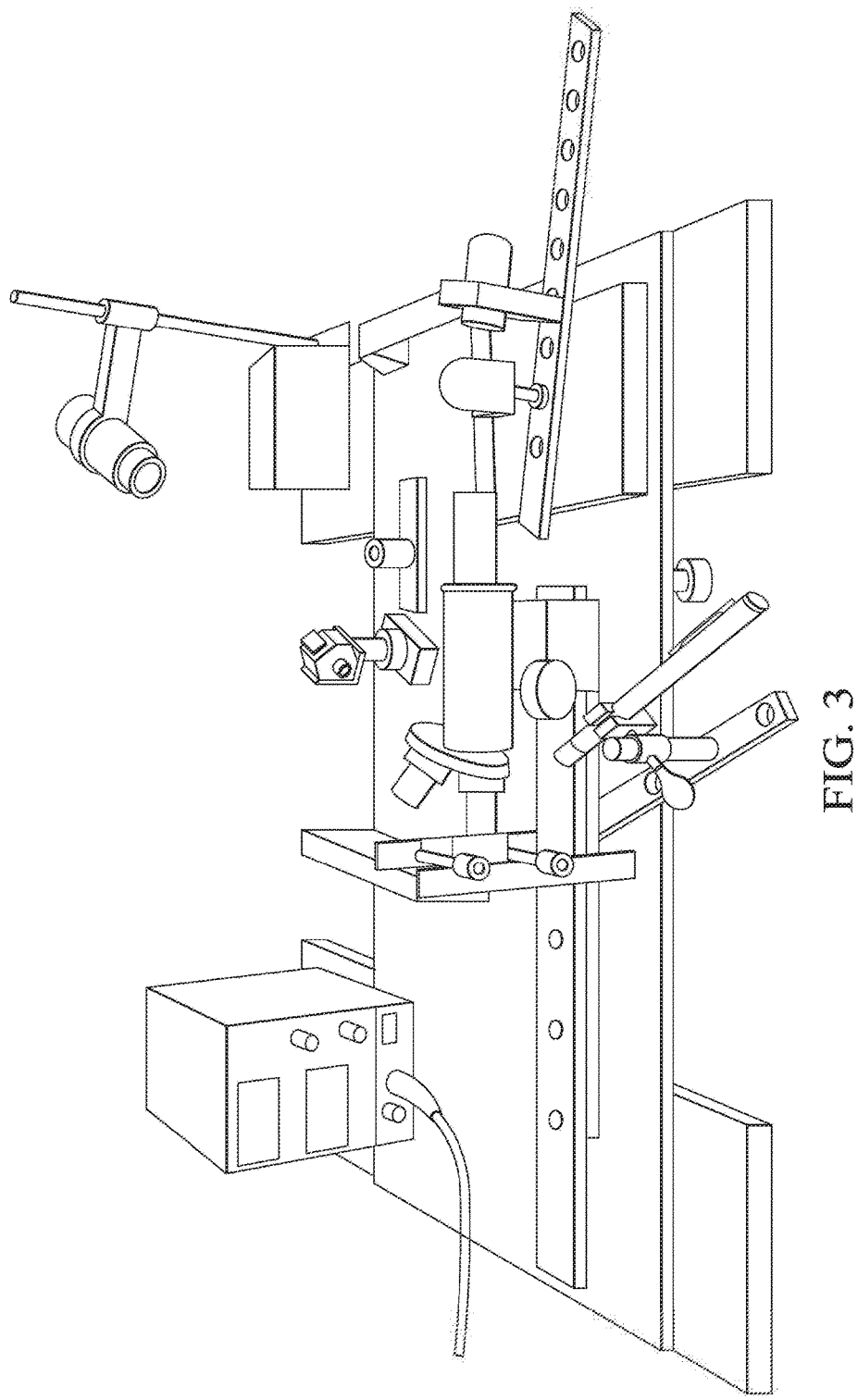
FIG. 3 provides a photograph of a bench-top device embodiment.
Figure 4:
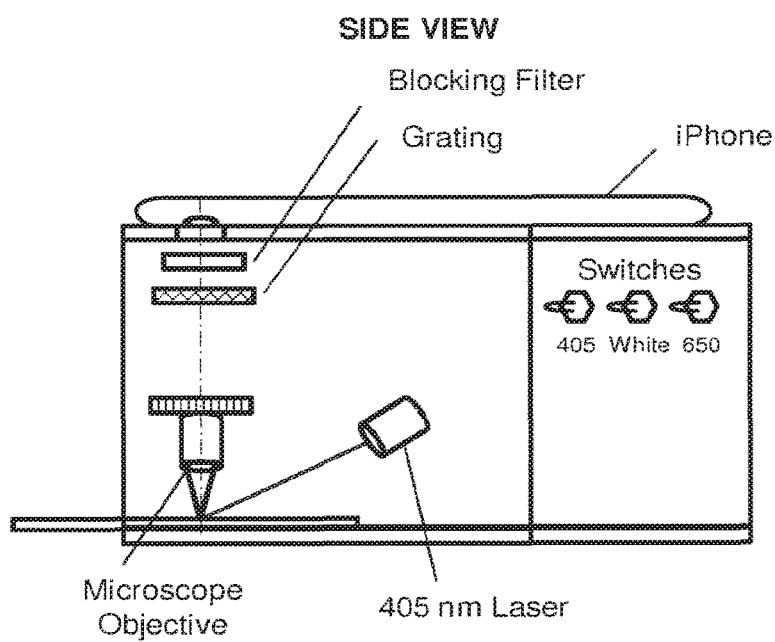
FIG. 4 provides a schematic illustration of a smartphone device embodiment.
Figure 5A:
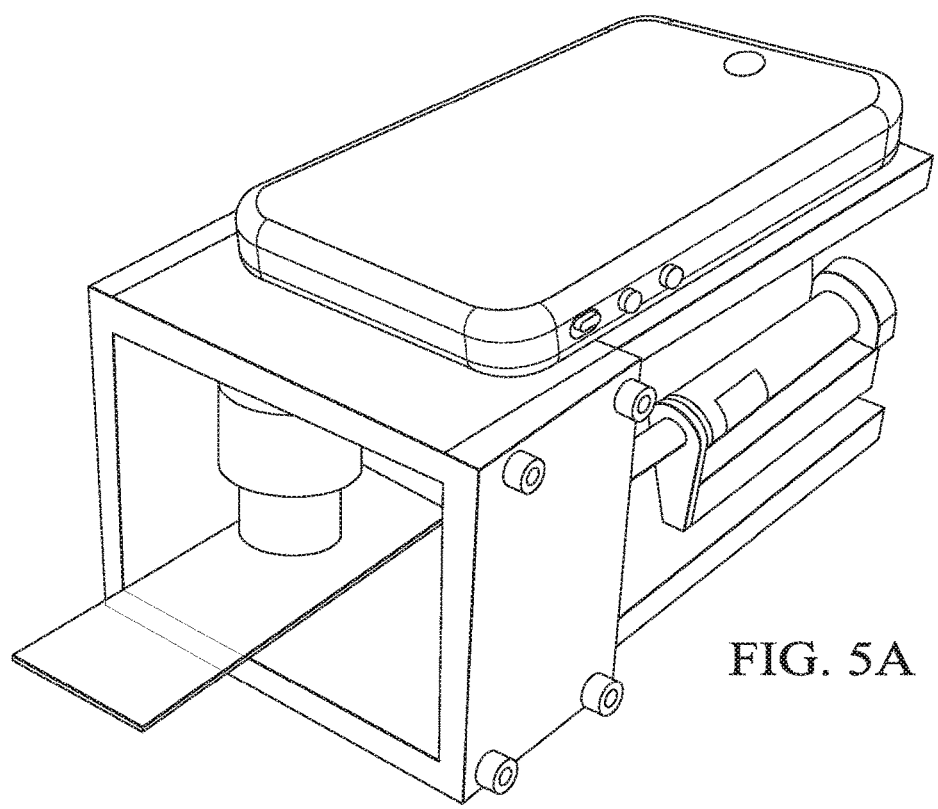
FIGS. 5A-B provides two photographs of a smartphone device embodiment, where a smart phone is shown on the top of the device with a slide underneath. Collection optics are shown in the foreground of 5A and are hidden within a case in 5B.
Figure 5B:
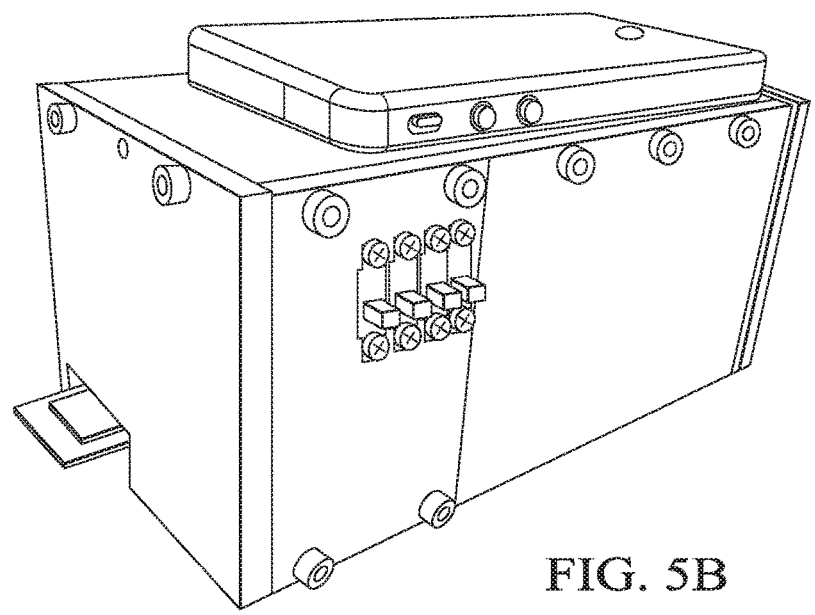

The "research instrument" embodiment is generally as described and depicted in FIG. 3. The "smartphone" embodiment takes the idea in a slightly different direction, as illustrated in FIGS. 4 and 5. This latter embodiment entails physical hardware (small microscope lenses, excitations sources, dispersive elements) that are attached to or are positioned to provide an image to a smartphone camera. Images captured by such devices are of sufficient resolution and magnification to be useful for characterization of fluorescence emission spectra. Benefits of using a smartphone for such detection is: (a) the ability to perform on-board analysis through applications written into the handheld computer, (b) utilization of integrated clock, GPS, and data transmission functions, and (c) the significant reduction in cost compared to most competing research-grade instruments. While most real-time bioparticle detectors cost more than $100,000, a smartphone-based bioparticle characterization system embodiment may cost less than $1,000, if not considerably less. This reduced cost, for example, allows for the fabrication of many instruments, thus allowing a huge increase in spatial information about bioparticle type and concentration if these instruments are spatially distributed. Further, the technology allows financially-challenged scientists, both those in funding-limited locations such as developing countries and other scientists, such as citizen scientists, without dedicated funding, to participate in the gathering of useful scientific data. Such a distribution may profoundly impact the understanding of bioparticle emissions and effects. Embodiments using a smart phone may incorporate excitation at 650 nm and/or 405 nm, auto-sampling on rolling tap, and auto-analysis using a smartphone algorithm.

Figure 2:
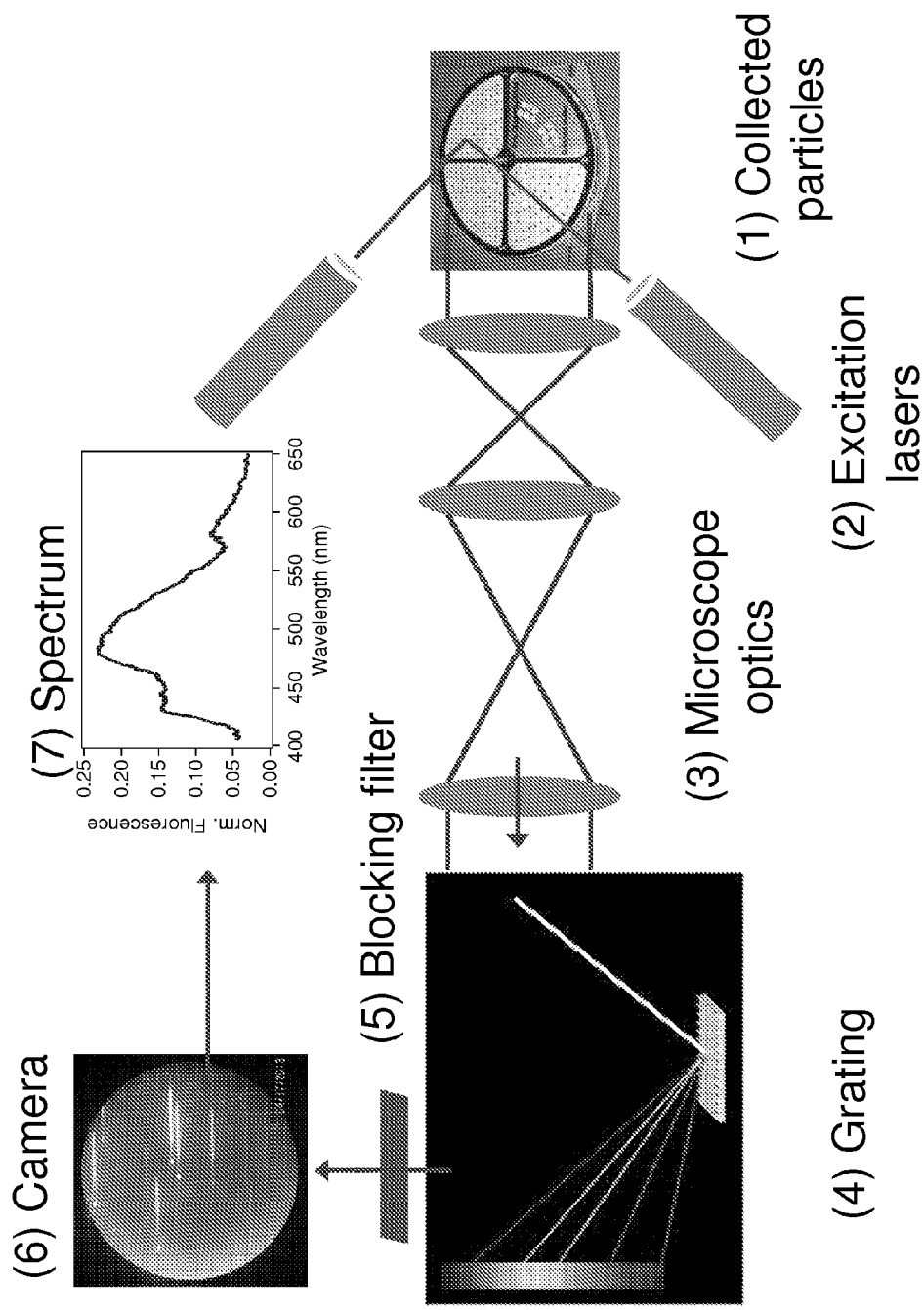
FIG. 2 provides a conceptual, schematic overview of a device embodiment.

In embodiments, devices of the invention comprise several components, schematically introduced by FIG. 2. (1) Small particles (e.g., 0.1-100 µm in size) are collected via impaction onto a plate. (2) Several small lasers are each focused onto the same spot on the impaction plate. (3) The scattered light (elastic/reflected or inelastic/fluorescence) is collected by simple microscope optics and directed onto a (4) grating that spectrally disperses the components of the light into discrete colors. The light is directed through an (5) optical filter and into the lens of a (6) camera. The filter is useful for blocking undesired wavelengths of light, as discussed below. The camera then records the image digitally and passes the information to (7) image processing software to extract fluorescence emission spectra. Each particle within the laser focus region on the impaction plate appears as bright dots of color (matching the excitation laser color) followed by a linear rainbow smear representing the fluorescence emission spectrum of that individual particle. The technique described allows an image processor to quickly recognize fluorescence spectra of many individual particles simultaneously, and with the optional aid of a clustering algorithm, for example, the spectra are optionally automatically compared to a database of standards for quick particle identification.

The use of multiple lasers/excitation sources is useful, for example, for two reasons. First, the camera detector records spectra as light intensity versus detector pixel, but this information needs to be calibrated into wavelength. To achieve this, simultaneously shining at least two lasers of known wavelength (e.g. 405 and 635 nm) allows for wavelength calibration. For this calibration, no blocking filters are utilized, allowing the reflected, elastic light scatter to be detected. Use of multiple laser excitation sources is also beneficial as the device is able to record full fluorescence emission spectra for every excitation source used. Using multiple lasers in sequence, and recording the emission spectra of each particle with each laser increases the information available for each particle. This is useful, for example, for revealing more fluorophores present in the interrogated particles. More specifically, the availability of additional emission spectra for each particle can increase the likelihood that comparisons with spectral standards listed in a database are able to uniquely identify a match with the particles interrogated. While interrogating the fluorescence emission spectra of particles by this technique, optical filters are useful for blocking elastic light scatter. This is beneficial as the elastic scatter can be orders of magnitude more efficient than inelastic scatter and this light may swamp the detection optics. During calibration these filters are moved out of the beam of light, but during emission spectra interrogation filters matching the wavelength of each excitation source are put in at appropriate times.

The above description has concerned the innovative use of the apparatus in measuring fluorescence spectra, which is a category of inelastic scattering characterized by a difference in energy (and wavelength) between the excitation light and the emitted light. Another use of the embodiments described herein is in determining elastic scattering spectra from individual particles in a collection simultaneously. Elastic scattering is characterized, for example, by no change in energy (wavelength) between incident and scattered light. The only change required to go from inelastic scattering measurements to elastic scattering measurements is, for example, removal of the blocking filter and replacement of the monochromatic laser with a continuous wavelength illumination source such as a tungsten white light or solar light source. The ability to measure elastic scattering of individual particles in this way provides benefits for the measurement of absorption coefficients, for example, which provide important information for aspects of atmospheric aerosol research. Further, extension to the measurement of elastic scattering provides for other areas for application of the device, such as in point-of-care medical devices. An example is given in the following paragraph.

In biomedical assaying, one commonly is interested in tagging a particular protein, for example, that is active in disease or as a biomarker signaling a propensity for disease, and having the tag report on the position and number density of the entity in question. As reported for example in the article by Schultz et al. ("Single-target molecule detection with nonbleaching multicolor optical immunolabels", PNAS, 97, #3, 996-1001, Feb. 1, 2000), nanoparticles of silver used as immunolabels have exceptionally bright elastic scattering peaks at different wavelengths based on size and shape of the Ag particles. When these labels have been attached to the molecules to be counted using antibody-coated silver particles, the elastic scattering peaks produce colored microscope images that can be detected as various colored particle images in a microscope, even with the unaided eye. Different sizes and shapes of silver particles produce scattering peaks at different wavelengths making possible the assaying of several different molecules at once, distinguished by the spectral peak positions. Schultz et al. have used bulky and sophisticated optical equipment to determine the spectra of individual Ag tags, with different colors distinguishing different molecules of interest. Use of the present smart-phone embodiment for single particle spectral measurements (in this case from elastic scattering rather than fluorescence), for example, brings this kind of powerful medical diagnostic technique into the doctor's office (point of care) rather than being limited to a hospital or clinical facility.

Other embodiments of the invention include the following modifications: (1) different placement and arrangements of the prism(s) including, but not limited to placing the prism in the eyepiece tube between objective lens and eye or camera lens, placing the prism between the eyepiece and camera, or multiple in-line prisms of alternating dispersion; (2) use of a grating for wavelength dispersion rather than prisms, such as a reflection grating or a transmission grating; (3) use of a horizontal microscope arrangement, for example, with components on an optical table for convenience in development and research.

Example 2: Fluorescent Particle Microscope

This example describes a technique for simultaneously taking low resolution spectra of many particles on a microscope slide. The immediate use of the technique is intended for distinguishing biological from non-biological particles among particles collected on slides or filters. However, the technique is also useful for microscopic analysis of any particle collection beyond commonly employed techniques for size, shape and polarization analysis. Examples include, but are not limited to, detection and identification of fungal spores and pollen, as done regularly by visual microscopic techniques for allergy reports, and for the detection and identification of toxic biogenic aerosol threats from terrorists or enemy combatants.

Figure 6:
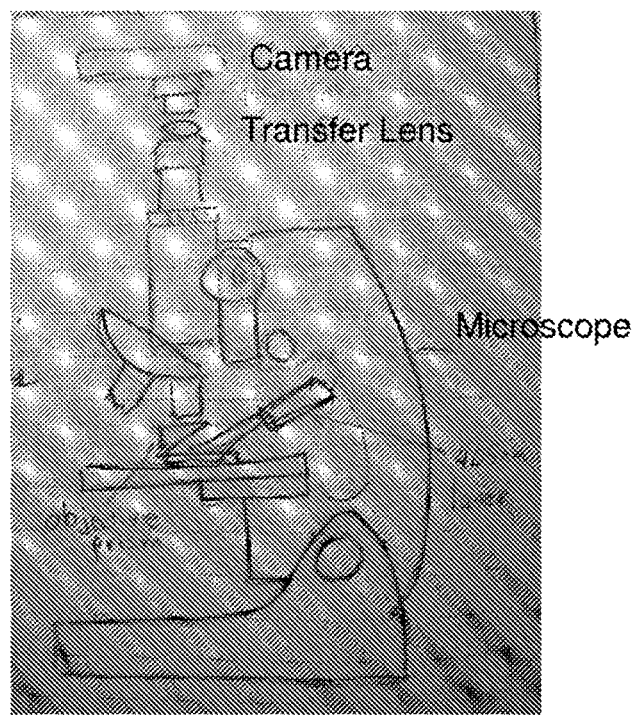
FIG. 6 provides a schematic illustration of a microscope-based device embodiment showing camera, transfer lens, microscope, objective prism and 405 nm laser components.

A basic embodiment is shown in FIG. 6, where a simple compound microscope is used to view and photograph the particles collected on microscope slides or filters, for example. The embodiment includes the use of a small-angle glass prism between the microscope's objective lens and the particle-carrying slide, which serves to disperse the light from each particle into its spectrum. Alternatively, the prism is optionally positioned between the eyepiece and the objective lens or above the eyepiece. The spectra of the many particles show up simultaneously to the eye or to the camera. In order to excite fluorescence in those particles that have this property, an excitation light source such as a uv or deep blue laser or light emitting diode (LED) is arranged to illuminate the particles at a low angle to their supporting surface, resulting in bright images of the particles and their fluorescent spectra against a dark background; that is, in dark field illumination. Optionally, a color image is obtained of a group of particles simply collected by settling on a glass slide, illuminated with a 20 mw diode laser of 405 nm wavelength. In some images, only a few particles show a fluorescence spectrum. For example, many are non-fluorescent particles which only show (elastic) scattering of the violet laser light. This, for example, shows how fluorescent and non-fluorescent particles can be easily distinguished, and the spectra of the former are available for analysis as indicated below.

Analysis of the spectral content of each particle's emission is optionally completed by an image analysis program such as Image-J, endorsed by the National Institutes of Health and available for download at no cost. For example, the spectrum of one of the particles is optionally plotted as light intensity on an arbitrary scale against pixel number along the direction of the dispersed spectrum. Further programming using the library of routines in Image-J is optionally automated to identify and count the number of both fluorescent (biological) and non-fluorescent particles as well as to determine their sizes and shapes and the fluorescent spectra of all particles.

Example 3: A Smartphone Spectrofluorometer for Environmental Research and Home Health Monitoring Micron-sized biological aerosol particles (e.g. bacteria, spores, pollen) suspended in air affect important environmental processes such as rain and snowfall and can severely impact public health. Detecting and differentiating biological particles amidst the slough of other airborne material is challenging and currently requires expensive instruments and costly analysis time. This example describes use of a smartphone platform based device for detection and characterization of biological particles at significantly lower cost than existing technologies (~$500 rather than >$100,000). The device has the potential to transform sub-fields of environmental research, for example, by multiplying worldwide data gathering by orders of magnitude, in part, by enabling citizen scientists to participate in cutting-edge research from wherever they are. The device utilizes the fact that its most expensive parts (sophisticated camera imaging, powerful computing, GPS positioning, instant results communication) are already in the hands of many millions of smartphone users. The device also has the potential to revolutionize allergen testing by enabling the cheap and rapid monitoring of exposure to mold spores and pollen. Lastly, variations of the device may be broadly applicable to clinical medical analyses, thus reducing costs and delays to patients.

The simple design will capture fluorescence spectra of various individual particles at a glance and comprises: (1) an aerosol impactor collection system (e.g. pump and microscope slide), (2) light sources (e.g. LED or laser diode) focused onto the collection slide, (3) light collection optics and dispersive grating, (4) smartphone camera, (5) smartphone analysis software.

The devices optionally include one or more of the following features (1) a sampling system for particle collection and impaction onto rolling tape; (2) use of cheap commercial components, machined materials and/or 3-D printed polymers for various components; (3) use of image analysis software within smartphone to compute line spectra on-board; and (4) use of cluster analysis and comparison to databases of standards to provide a secondary analysis by comparing particle spectra with the database for particle identification Example 4: Development of a Hand-Held Fluorescence Micro-Spectrometer for Simultaneous Multiple Particle Detection Fluorescence provides a useful technique for bioaerosol characterization. For example, various commercial instruments use fluorescence for aerosol detection, such as single-particle detection in real-time. However, no currently available instrument provides full emission spectra of multiple detected particles simultaneously. Fluorescence microscopy, however, is a well utilized technology capable of simultaneous analysis of single particles, though emission is generally only detectable via select wavelength filters. Fluorescence spectroscopy provides a technique for obtaining detailed spectroscopic information, though only bulk analysis is generally available and it is not possible to obtain information for single particles individually. Thus, fluorescence spectroscopy masks the properties of a minority of particles mixed into a large matrix of other particles, and little information can be gained about particles in trace concentrations that can have large health and environmental impacts.

In contrast, the present Example provides for an inexpensive instrument capable of simultaneously characterizing fluorescence emission spectra from many individual particles each at several excitation wavelengths. An overview of a device embodiment is depicted in FIG. 2. This embodiment is conceptually similar to a laser-scanning microscope but includes a dispersive element to allow for detection of emission spectra of multiple particles simultaneously.

Smartphone embodiment. The smartphone embodiment of a particle fluorescence spectrometer is illustrated in FIG. 4. This embodiment includes all of the same features as the bench-top or lab embodiments, but in a smaller, less expensive configuration. This embodiment enables expanded spatial sampling and "citizen science," for example, by providing an affordable device. Embodiments include dual fluorescence excitation wavelengths including 650 nm and 405 nm, though other embodiments optionally include additional excitation wavelengths. Various embodiments optionally include auto-sampling onto rolling tape, auto-analysis via smartphone algorithm, transfer of collected images to remote locations for analysis and particle identification. These aspects enable days of unmonitored analysis.

Figure 7:
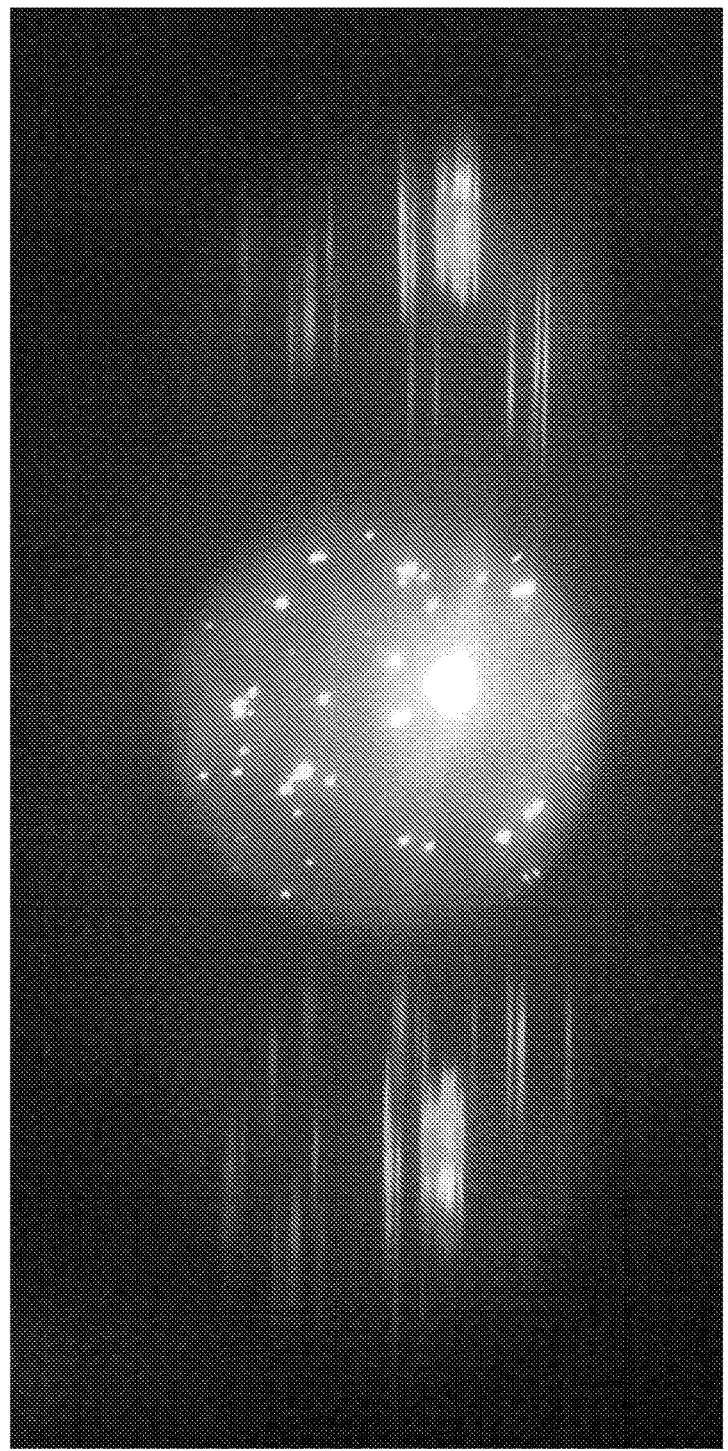
FIG. 7 provides an image of collected fluorescence imaged by a smartphone device embodiment, where the center image is the standard microscope image and the color swaths on either side are images dispersed by the grating in first order diffraction with the dispersion in the left and right images being mirror images of one another.
Figure 8:
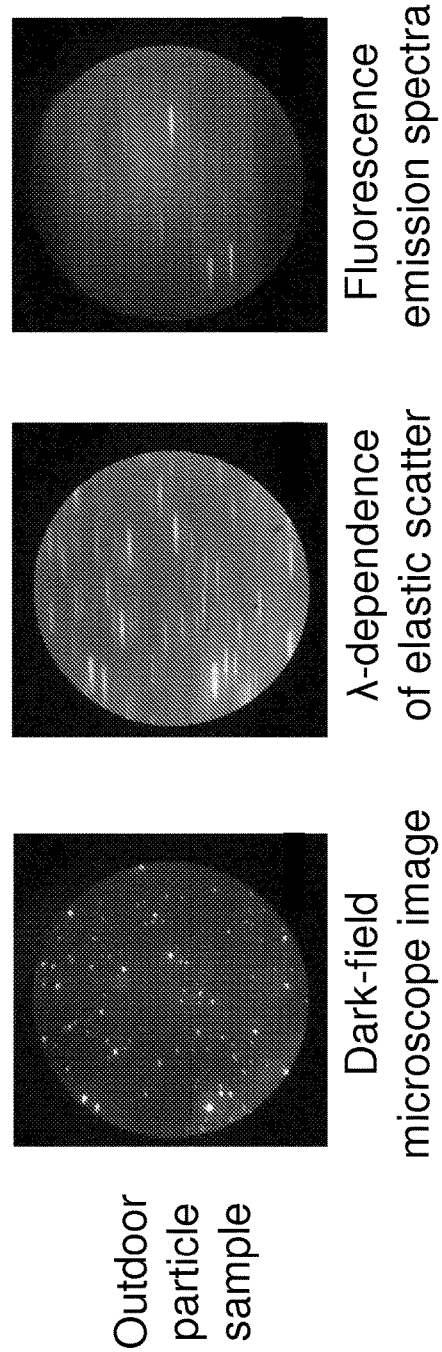
FIG. 8 provides three images of the same set of particles collected onto a glass substrate and illuminated separately: dark field microscope image (left), an image depicting the wavelength dependence of elastic scatter (middle), and an image of fluorescence from particles collected in an outdoor environment (right). Fluorescent image (right) shown using excitation blocking filter. Note that there are numerous particles that show elastic scattering but only two that clearly show inelastic scattering (fluorescence).

The embodiments described herein uniquely provide for the ability to (1) simultaneously look at many particles, (2) obtain full emission spectra (and comparison of fluorescent vs non-fluorescent particles), (3) analyze particles using multiple analysis techniques including a combination of microscope images, elastic scattering spectra and fluorescence spectra, (4) obtain spectra at several excitation wavelengths and utilize cluster algorithm for analysis and characterization using an inexpensive platform that is optionally automated. In addition, using a smartphone is beneficial as these devices provide not only computer processing capabilities and camera optics, but also wireless communication for remote storage and analysis of the images and data obtained and the ability to attach a GPS location to the images and data obtained. Example particle scatter images collected using embodiments of the invention are depicted in FIGS. 7 and 8.

Figure 9:
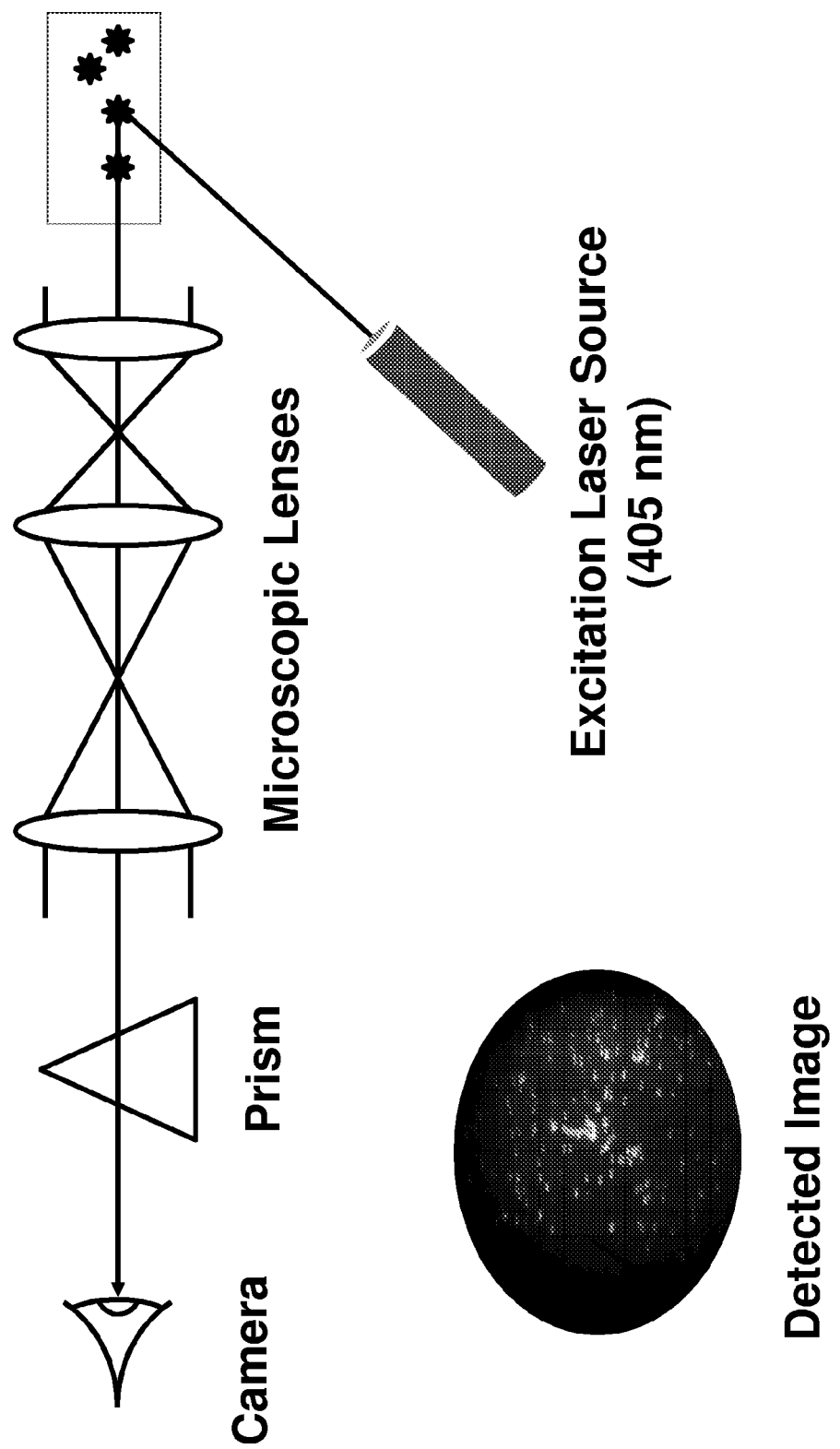
FIG. 9 provides a schematic diagram showing optical elements used in embodiments of the invention. An example detected image is shown in the lower left, with blue light excitation and no blocking filter.
Figure 10:
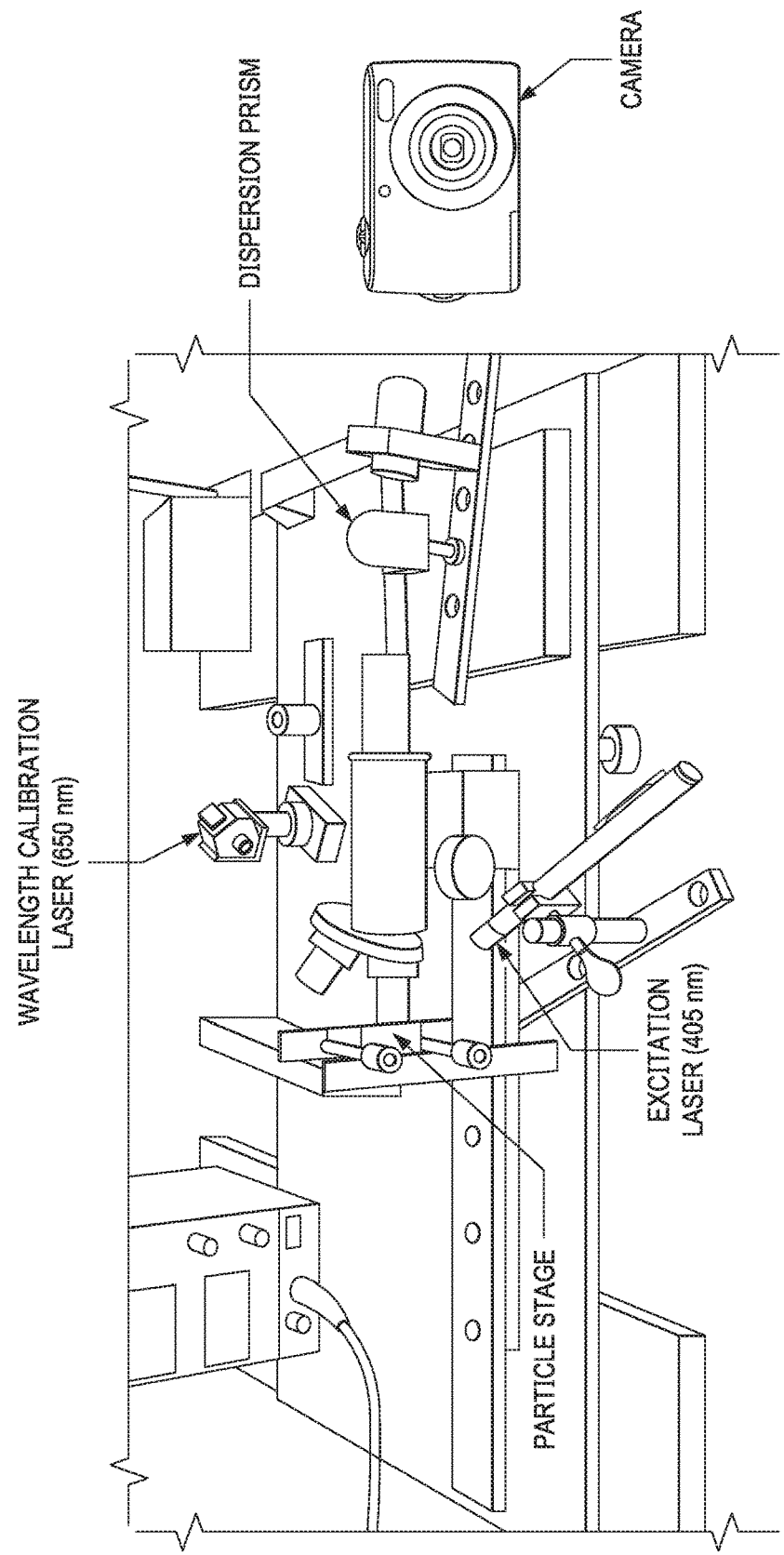
FIG. 10 provides an expanded image of the bench-top device embodiment shown in FIG. 3 and illustrates various components. The camera detector is off the image to the right, but a vendor image of the model used is shown. Note that the blocking filter (blocking <430 nm) was not inserted for the images in this picture.
Figure 11:
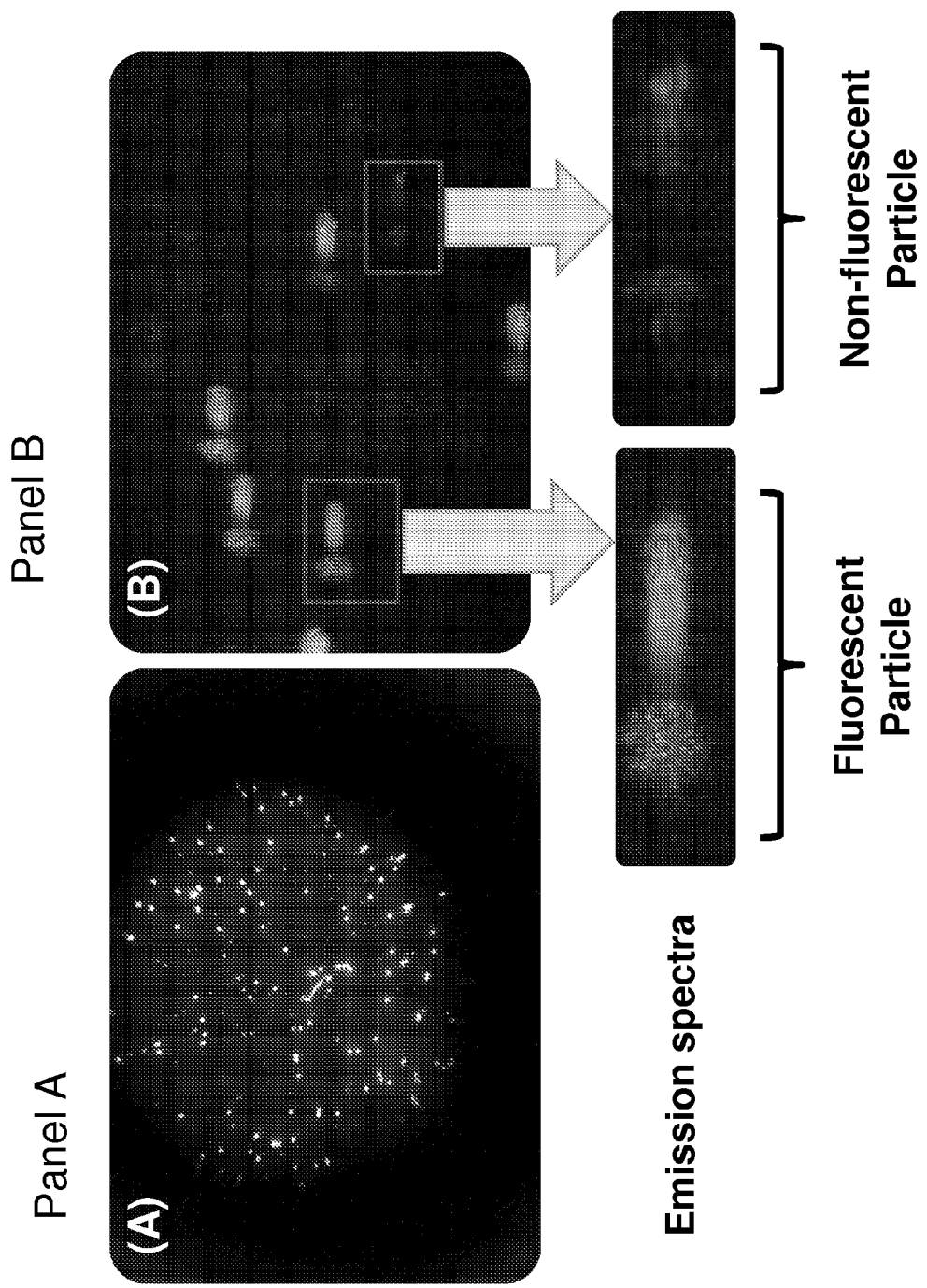
FIG. 11 provides two images of a set of particles collected on a glass substrate. Panel (A) shows a standard microscope image with white light illumination and panel (B) shows a magnified image of the same particles excited with blue laser light with scattered light dispersed into emission spectrum and shown without a blocking filter. Two example color swaths, or emission spectra are shown at the bottom right and highlight the visual difference between fluorescent and non-fluorescent particles.

Example 5: Bio-Imaging and Fluorescence Analysis of Primary Biological Aerosol Particle FIG. 9 illustrates a schematic overview of a microscope for imaging of fluorescence from multiple biological aerosol particles using a 405 nm excitation laser. FIG. 10 depicts an expanded view of a bench-top embodiment of a fluorescence spectrometer showing the particle collection stage, the wavelength calibration and excitation lasers, the dispersion prism and detection camera. FIG. 1I provides images of visible light scattered from lycopodium and other particles and illustrates a comparison between fluorescent particles and non-fluorescent particles.

Example 6: Particle Detection Using a Black and White Camera

The invention includes a wavelength dispersive microscope spectrofluorometer incorporating a black and white camera for acquiring images of scattered and/or emitted light. Potential benefits achieved using a black and white camera for imaging include an expanded wavelength range to about 1000 nm because of the absence of an infrared blocking filter and avoidance of spectral features from color pixels. FIGS. 12A and 12B provide spectra of grass pollen particles. FIG. 12A provides results corresponding to particles from *Poa pratensis* (Kentucky bluegrass) using a wavelength dispersive microscope spectrofluorometer incorporating a black and white camera (top plot) and a color camera (bottom plot). FIG. 12B provides results corresponding to particles from *Anthoxathum odoratum*, as an example of another type of grass pollen, as reported by O'Connor et al. 2014. The prominent peak in FIGS. 12A and 12B at about 680 nm corresponds to chlorophyll. This example shows the agreement possible between the simplified wavelength dispersive microscope spectrofluorometer of this invention and the more common, but much bulkier and more expensive method usually employed in FIG. 15B.

Example 7: Use of a Reflection Grating in a Simplified Arrangement for a Conventional Microscope Systems and methods of the invention may utilize a variety of wavelength dispersive elements placed in optical communication with the particles supported by the substrate. For example, the dispersive element shown in FIG. 6 is a prism provided between the objective lens of the microscope and the substrate having particles and the dispersive element shown in FIG. 1E is a transmission grating provided between the objective lens of the microscope and the substrate having particles. The invention also provides systems and methods, however, wherein the wavelength dispersive element is a reflection grating placed in optical communication with the particles, for example, provided under a microscope objective lens with particulate-sample-slide positioned between the grating and the objective.

FIGS. 13 and and 13A-13C provide photographs and schematic diagrams showing a system of the invention utilizing a dispersive element comprising a reflection grating provided beneath, and in optical communication with, a microscope slide serving as a substrate for supporting particles under analysis. The microscope slide is maintained at a fixed distance from the reflection grating which is also provided in optical communication with a microscope. In the embodiment shown in FIGS. 13 and 13A-C, for example, the microscope slide supporting the particles is provided in optical communication with, and between, the reflective grating and the microscope. FIG. 13 shows a side view of the slide and reflective grating assembly. FIG. 13A shows the microscope in optical communication with the slide and reflective grating assembly. FIG. 13B shows a close up view of the slide and reflective grating assembly comprising a microscope slide and reflective grating. FIG. 13C provides a schematic showing a top view of the slide and reflective grating assembly. As shown in FIG. 13C, particles under analysis are provided on the external side of the microscope slide which is provided in optical communication and maintained at a selected distance from the reflective grating. In operation, the particles are illuminated by an optical source (e.g., white light source, laser, LED source, etc.), thereby generating scattered and/or emitted light from the particles. The scattered and/or emitted light interacts with the reflection grating so as to generate wavelength dispersed reflected light that is collected by the collection optics of the microscope. In an embodiment, the light collected by the collection optics of the microscope is imaged on to a digital imaging device, such as a CCD sensor or a CMOS sensor.

Figure 13:
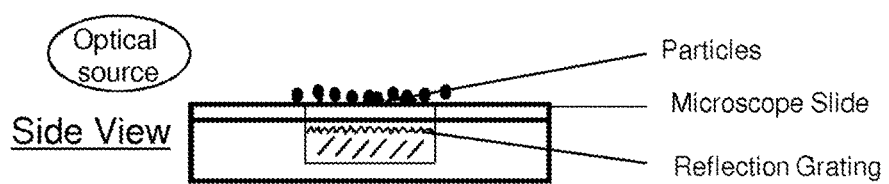
Figure 13A:
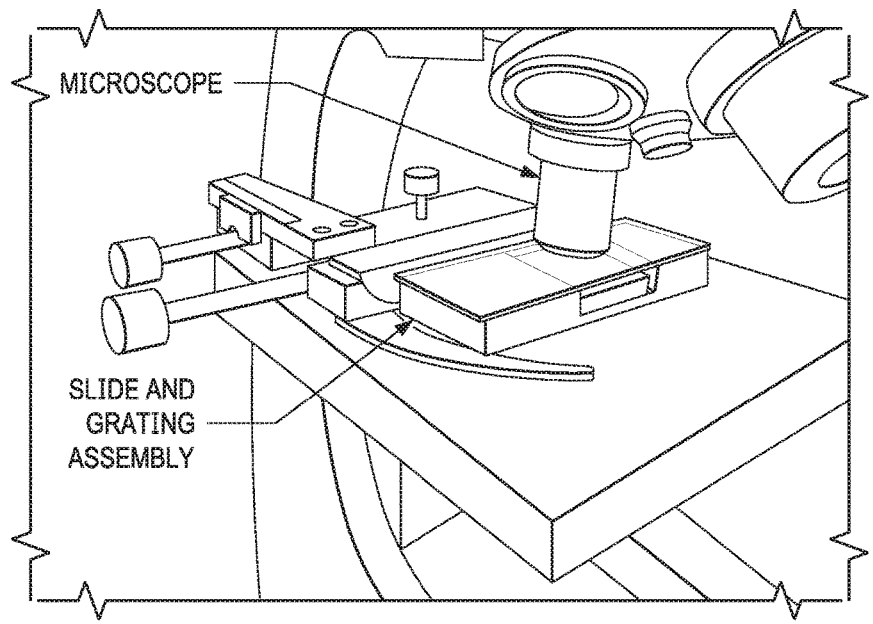
Figure 13B:
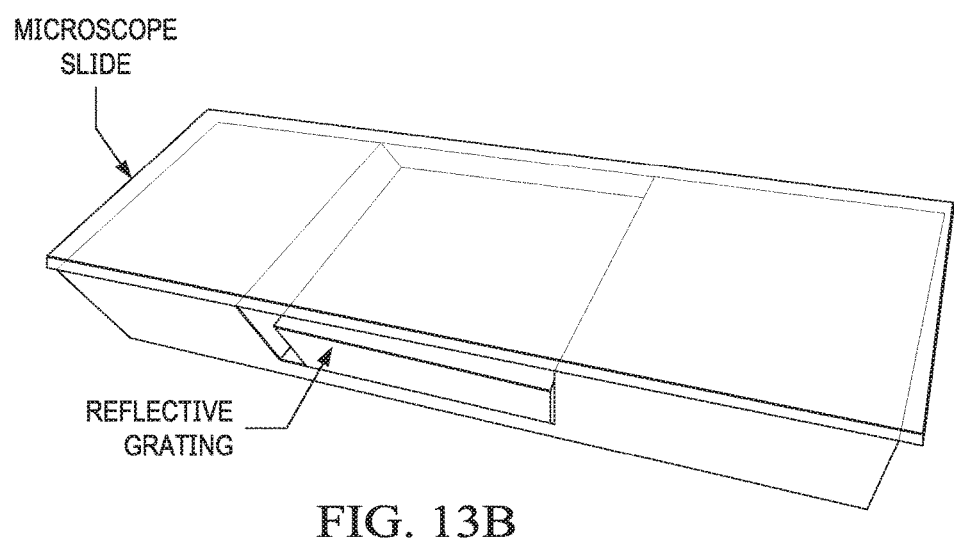
Figure 13:
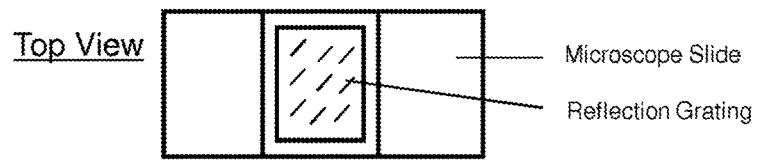

In some embodiments, the assembly illustrated in FIG. 13C is sized to fit into the x-y positioning stage of a common microscope. In an embodiment, the reflective grating and substrate can replace the transmission dispersion element in any of the systems as described herein. Addition of one or more optical sources in optical communication with the particles on the microscope slide (e.g., on or in the vicinity of the microscope stage, see e.g., FIG. 13C), such as white light sources, pulsed or CW laser diodes and LEDs, complete the conversion of a standard camera-equipped transmission microscope for use as a microscope particle spectrofluorometer described in this document. This assembly also provides a system of the present invention and can be used to efficiently transform any microscope into a wavelength dispersive microscope spectrofluorometer In Example 3 a simple and inexpensive instrument was described based on detection of particle spectra and possible data analysis by a smart phone. An example of the use of the objective lens-reflecting grating arrangement of FIG. 13 in such an inexpensive implementation is the use of a section of a DVD or CD disc wherein the disc comprises both a surface for the particles which are to be analyzed, separated at a fixed distance from a reflectance grating, all produced during the manufacture of the DVD or CD disk.

FIGS. 14A-C provide schematics of systems of the present invention using a DVD or CD disc as an integrated substrate and reflective grating wavelength dispersive component. FIG. 14A provides a top view of the CD or DVD having particles provided on an external surface. FIG. 14B provides a side view showing the particles supported by the external surface of the CD or DVD and also showing the reflective grating component provided in optical communication with the particles. FIG. 14C provides a side view showing incorporation of a microscope provided in optical communication with the CD or DVD so as to receive reflected light from the reflective grating. FIG. 14C also shows incorporation of one or more optical sources for illuminating the particles supported by the external surface of the CD or DVD.

As shown in FIGS. 14A-C, the mirror surface of the second surface from the top of the disk forms a virtual image of each particle below the reflecting surface. Optical rays from this virtual image travel upward through the microscope optics and are spectrally dispersed by the grating just as they would be in the case of particles on the surface of a slide travelling upward through a transmission grating. This arrangement eliminates the need for a separate transmission grating, which is the most expensive component of a smart phone instrument such as that in FIG. 5. It can make the smart phone camera even simpler and less expensive to manufacture making possible its distribution much more widespread than is possible for much more expensive and larger instruments previously used.

Figure 15:
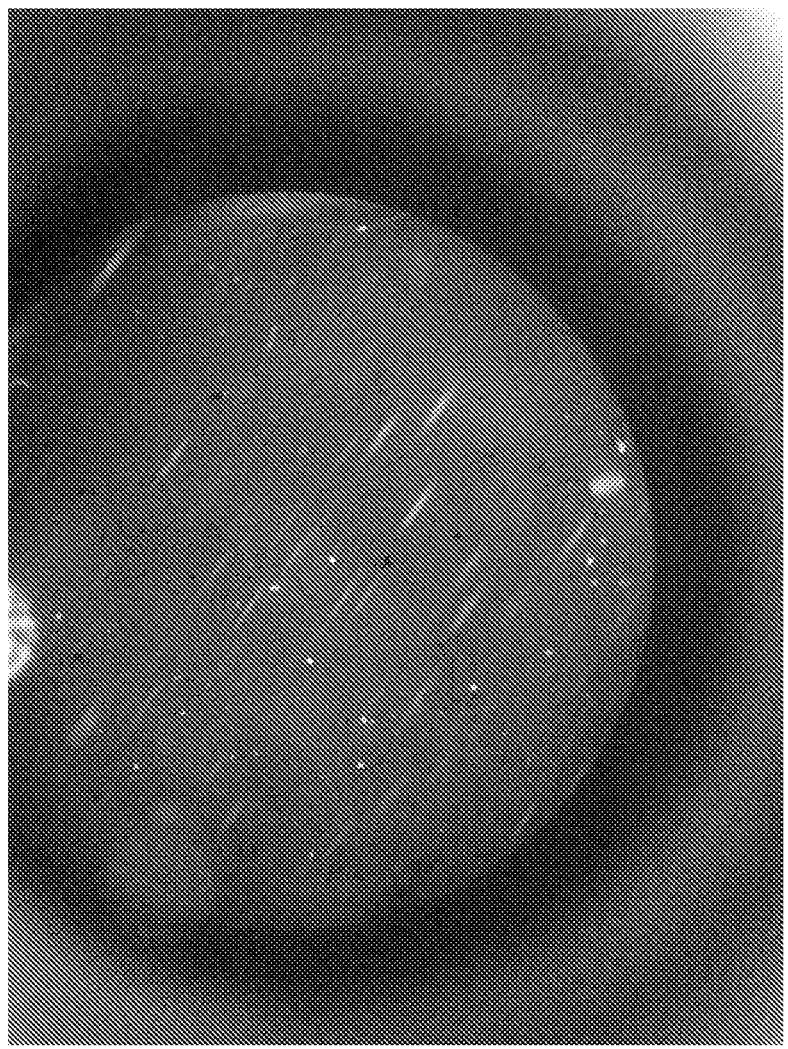
FIG. 15 shows an image obtained with the smartphone prototype using lycopodium particles deposited onto a CD as both substrate and reflection dispersive element.

FIG. 15 shows an image taken with the smartphone prototype using lycopodium particles deposited onto a CD as both substrate and reflection dispersive element.

Example 8: Combining Three Different Analytical Techniques in One Instrument

Aspects of the invention provides a new technique for determining the spectra of individual particles in a collection of microscopic particles using a simple monochromator system that bypasses the need for using an entrance slit for each particle. Each particle effectively acts as its own entrance slit. Various excitation sources such as lasers and LEDs can comprise the excitation sources for determining both elastic and inelastic scattering spectra. By using even more varied excitation strategies, the spectrophotometry system as described can bring other analytical tools to the same instrument. This Example describes two additional techniques useful in the present methods and systems laser induced breakdown spectroscopy (LIBS) and Raman scattering.

LIBS uses a highly focused laser beam to ablate a substance in a spatial region where the plasma formed by the ablation can produce atomic emission spectra characteristic of the atomic elements in the sample. In typical LIBS systems that have been employed for small particle analysis, a pulsed Nd:YAG laser is often employed. In the present embodiment, the emitted light produced in the laser induced breakdown is analyzed by the single particle microfluorometer described herein.

Another technique that can be employed with the same spectrophotometric system is Raman spectroscopy. In this technique, light from an excitation laser source, usually in the visible or near infrared spectral region, is frequency-shifted by interaction with vibrational modes of the sample. This frequency-shifted light is detected as the Raman signal, which gives information about vibrational modes. Raman spectrophotometers commonly focus the inelastically scattered light onto the slit of a monochromator for wavelength analysis detected by a detector. If the monochromator scans in wavelength, a detector such as a photomultiplier tube can be used. For a fixed position of the dispersing element (such as a grating) a multipixel array detector (such as a CCD or any of the detectors described in previous examples of this device) can be used to detect and analyze the spectrum without any mechanical scanning in wavelength. In contrast to these methods of analysis, the wavelength dispersive microscope spectrofluorometer of certain embodiments uses the objective lens of a microscope arrangement to collect and image each and every particle in the field of view onto an array detector, with a dispersing grating or prism somewhere in the light path between particle and detector.

The ability to use three different excitation sources incident on particles on a substrate, with the same slitless monochromator used for all three different spectra, can provide much more information than any single excitation source would provide. Fluorescence spectra give information about the biological nature of particles, LIBS gives information about the atomic nature of the particles, and Raman spectra give information about the molecular nature of the particles—all on the same particle in a collection of particles. It is also possible that one or more of the excitation sources can be used for more than one purpose. For example, a Nd:YAG laser might be used for both fluorescence excitation and LIBS excitation

REFERENCES

Edwards, U.S. Pat. No. 4,918,475; Apr. 17, 1990; "Camera with Spectroscope Attachment"

Karnaukhov et al., U.S. Pat. No. 4,354,114; Oct. 12, 1982, "Apparatus for Investigation of Fluorescence Characteristics of Microscopic Objects"

O'Connor, D. J., Lovera, P., Iacopino, D., O'Riordan, A., Healy, D. A. and Sodeau, J. R.: Using spectral analysis and fluorescence lifetimes to discriminate between grass and tree pollen for aerobiological applications, Analytical Methods, 6, 1633-1639, 10.1039/c3ay41093e, 2014.

Roshchina et al., Nov. 6, 2004, "Autofluorescence of Developing Plant Vegetative Microspores Studied by Confocal Microscopy and Microspectrofluorimetry," Journal of Fluorescence, Vol. 14, No. 6.

Schultz et al. ("Single-target molecule detection with non-bleaching multicolor optical immunolabels, PNAS, 97, #3, 996-1001, Feb. 1, 2000).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of simultaneously measuring scattering or emission spectra of a plurality of particles, the method comprising the steps of:
   providing said plurality of particles;
   exposing said plurality of particles to electromagnetic radiation from an optical source, wherein all of said plurality of particles are simultaneously exposed to electromagnetic radiation from said optical source and wherein interactions between each particle and said electromagnetic radiation from said optical source generates scattered or emitted electromagnetic radiation from each particle;
   collecting and directing at least a portion of said scattered or emitted electromagnetic radiation from each particle onto a wavelength dispersive optical element, thereby generating spatially dispersed scattered or emitted electromagnetic radiation from each particle;
   detecting at least a portion of said spatially dispersed scattered or emitted electromagnetic radiation from each particle using a digital imaging device, thereby generating a digital image of said spatially dispersed scattered or emitted electromagnetic radiation from each particle; and
   analyzing said digital image to obtain a scattering or emission spectrum of each particle, thereby generating a plurality of scattering or emission spectra corresponding to said plurality of particles, and for each particle,
      determining whether the particle is fluorescent or non-fluorescent based on the scattering or emission spectrum of each particle, and
      obtaining a scattering or emission spectrum of each fluorescent particle;
   displaying, through the digital imaging device, non-fluorescent particles as single dots and fluorescent particles as rainbow smears of color based on the scattering or emission spectra of the non-fluorescent and fluorescent particles,
      wherein said digital imaging device comprises a mobile electronic device or a handheld electronic device.

2. The method of claim 1, wherein said method does not include a step of passing said scattered or emitted electromagnetic radiation from each particle through an entrance slit.

3. The method of claim 1, wherein each of said plurality of particles functions as a point source of scattered or emitted electromagnetic radiation, thereby eliminating a need for an entrance slit.

4. The method of claim 1, wherein said scattering or emission spectrum is a fluorescence spectrum, a Raman spectrum or LIBS spectrum of each fluorescent particle.

5. The method of claim 1, wherein said analyzing step comprises, for each particle, assigning a wavelength value and an intensity value to a plurality of pixels of said digital image, wherein each pixel in said plurality of pixels represents detection of spatially dispersed scattered or emitted electromagnetic radiation from that particle.

6. The method of claim 1, wherein said analyzing step comprises obtaining one or more additional digital images of spatially dispersed elastically or inelastically scattered electromagnetic radiation from said plurality of particles and, for each particle, assigning wavelength values to one or more pixel locations corresponding to detection of spatially dispersed elastically or inelastically scattered radiation from that particle, thereby obtaining wavelength reference points for each of said plurality of scattering or emission spectra corresponding to said plurality of particles.

7. The method of claim 1, wherein said wavelength dispersive optical element spatially disperses incident scattered or emitted electromagnetic radiation along one direction as a function of wavelength, and wherein said step of analyzing comprises, for each particle, determining an intensity value and/or a wavelength value for each of a plurality of pixels in said digital image representing detection of spatially dispersed scattered or emitted electromagnetic radiation distributed along said direction.

8. The method of claim 1, wherein said wavelength dispersive optical element is a transmissive wavelength dispersive optical element or a reflective wavelength dispersive optical element provided in optical communication with said particles.

9. The method of claim 1, further comprising, after said analyzing step, comparing said scattering or emission spectrum of each particle with a reference database of scattering or emission spectra of known or standard particles to determine a characteristic of each particle, wherein said characteristic is selected from the group consisting of: a particle composition, a particle type, particle size, particle shape, particle morphology, particle optical properties, particle physical properties and any combination of these.

10. The method of claim 1, wherein said plurality of particles comprises one or more particle types selected from the group consisting of: biological particles and biological particle fragments, pollen and pollen fragments, dust, soot, ash, road dust, mold spores, fungal spores, archae, viruses, algae, cyanobacteria, biological crusts, lichen, bacterial cells and cell fragments, fungal cells and cell fragments, liquid organic particles, solid organic particles, gel organic particles, mixed phase organic particles, inorganic particles, mixed composition particles, mineral particles, soil-derived particles, marine-derived particles, sea salt particles, aerosols, fluorescent particles, non-fluorescent particles, manufactured particles, metal nanoparticles, gold nanoparticles, silver nanoparticles, medical assay particles, labeled particles, tagged particles and any combinations of these.

11. The method of claim 1, wherein said step of providing said plurality of particles comprises providing said plurality of particles in a fluid, wherein said fluid comprises a liquid, a gas, air, oxygen gas, nitrogen gas, liquid water, water vapor, a salt solution, a buffer solution, a bodily fluid, blood, plasma, an organic solvent, an inorganic solvent or any combination of these.

12. The method of claim 1, wherein said step of providing said plurality of particles comprises providing a substrate and collecting said plurality of particles on said substrate, wherein said plurality of particles are collected on said substrate by settling said plurality of particles on said substrate, by impacting said plurality of particles on said substrate, or by filtering said plurality of particles on said substrate, and wherein said substrate comprises a transparent substrate, a non-transparent substrate, a coated substrate, an uncoated substrate, a reflective substrate, or an opaque substrate.

13. The method of claim 12, wherein said substrate comprises glass, plastic, adhesive, adhesive tape, metal, Teflon, polymer, quartz, diamond, sapphire, a crystal, a particle filter, compact disc (CD), digital video disc (DVD), blu-ray disc, mirror, dispersive element, non-dispersive element, reflective grating, or any combination of these.

14. The method of claim 1, wherein said optical source comprises two or more sources and said exposing, collecting and directing, detecting, and analyzing steps are repeated two or more times such that two or more scattering or emission spectra for each particle are obtained, wherein each of said two or more scattering or emission spectra for each particle correspond to detection of scattered or emitted electromagnetic radiation generated by one of said two or more sources.

15. The method of claim 1, wherein said optical source comprises a continuous source.

16. The method of claim 1, wherein said scattered or emitted electromagnetic radiation comprises at least one of inelastically scattered electromagnetic radiation, fluorescence, elastically scattered electromagnetic radiation, Raman scattered electromagnetic radiation and LIBS electromagnetic radiation.

17. The method of claim 1, further comprising, prior to the detecting step, a step of filtering said spatially dispersed scattered or emitted electromagnetic radiation from each particle, thereby generating filtered spatially dispersed scattered or emitted electromagnetic radiation from each particle, wherein said detecting step comprises detecting at least a portion of said filtered spatially dispersed scattered or emitted electromagnetic radiation from each particle using said digital imaging device, thereby generating said digital image.

18. The method of claim 17, wherein said filtering step comprises interacting at least a portion of said dispersed scattered or emitted electromagnetic radiation with an optical filter, wherein said optical filter is a lonqpass filter, a bandpass filter, a notch filter, an interference filter, a reflective filter, a transmissive filter, a diffraction filter or a dichroic filter.

19. The method of claim 1, wherein said wavelength dispersive optical element comprises a grating or a prism.

20. The method of claim 1, wherein said mobile electronic device or said handheld electronic device comprises a smartphone or a tablet.

21. The method of claim 1, wherein said analyzing step is completed using said mobile electronic device or said handheld electronic device.

22. The method of claim 1, further comprising, after said analyzing step, transmitting said digital image to a remote computer, a cloud computing system or a distributed computing system using a transceiver of said mobile electronic device or said handheld electronic device and wherein said analyzing step is completed using said remote computer, said cloud computing system or said distributed computing system.

23. A system for simultaneously measuring scattering or emission spectra from a plurality of particles, the system comprising:
an optical source for generating electromagnetic radiation;
a substrate or liquid volume for providing said plurality of particles, wherein said substrate or liquid volume is positioned to receive electromagnetic radiation from said optical source and wherein interactions between each particle and said electromagnetic radiation from said optical source generates scattered or emitted electromagnetic radiation from each particle;
a wavelength dispersive optical element for generating spatially dispersed scattered or emitted electromagnetic radiation from each particle, said wavelength dispersive optical element positioned to receive at least a portion of said scattered or emitted electromagnetic radiation from each particle;
a processor for:
analyzing said digital image corresponding to detection of said spatially dispersed scattered or emitted electromagnetic radiation from each particle and for obtaining a scattering or emission spectrum of each particle, thereby generating a plurality of scattering or emission spectra corresponding to said plurality of particles,
and for each particle,
determining whether the particle is fluorescent or non-fluorescent based on the scattering or emission spectrum of each particle and
obtaining a scattering or emission spectrum of each fluorescent particle,
a digital imaging device for generating a digital image of said spatially dispersed scattered or emitted electromagnetic radiation from each particle, said digital imaging device positioned to receive at least a portion of said spatially dispersed scattered or emitted electromagnetic radiation from each particle,
wherein non-fluorescent particles appear as single dots and fluorescent particles as rainbow smears of color based on the scattering or emission spectra of the non-fluorescent and fluorescent particles; and
wherein said processor is provided in data communication with said digital imaging device, and
wherein said digital imaging device comprises a mobile electronic device or a handheld electronic device.

24. The system of claim 23, wherein said system does not include an entrance slit positioned between said plurality of particles and said wavelength dispersive optical element.

25. The system of claim 23, wherein each of said plurality of particles functions as a point source of scattered or emitted electromagnetic radiation, thereby eliminating a need for an entrance slit.

26. The system of claim 23, wherein said mobile electronic device or said handheld electronic device comprises a smartphone or a tablet.

27. The system of claim 23, further comprising wherein said mobile electronic device or said handheld electronic device comprises a wireless transceiver providing data communication with said processor, wherein said processor comprises a remote computer, a cloud computing system or a distributed computing system.

28. The system of claim 23, wherein said wavelength dispersive optical element is a transmissive wavelength dispersive optical element or a reflective wavelength dispersive optical element provided in optical communication with said particles, and wherein said processor is provided in said mobile electronic device or said handheld electronic device.

29. The system of claim 23, further comprising one or more optical elements each independently positioned in optical communication with one or more of said optical source, said particles, said substrate, said liquid volume, said wavelength dispersive optical element and said digital imaging device, wherein said one or more optical elements are each independently selected from the group consisting of: a lens, a mirror, a partial reflector, a filter, a beam splitter, an optical fiber, an optical waveguide, an optical beamguide, a window, an aperture, a slit, a prism, a grating, a reflective grating, a polarizer, a wave plate, a crystal and a beam homogenizer.

30. The system of claim 23, wherein the optical source is interchangeable and the wavelength dispersive optical element is removable and interchangeable.

\* \* \* \* \*